US011058349B2

(12) United States Patent
Sagiv et al.

(10) Patent No.: US 11,058,349 B2
(45) Date of Patent: Jul. 13, 2021

(54) NON-INVASIVE HANDLING OF SLEEP APNEA, SNORING AND EMERGENCY SITUATIONS

(71) Applicants: Ovadia Sagiv, Kiron (IS); Moshe Hayik, Hod Ha-Sharon (IS)

(72) Inventors: Ovadia Sagiv, Kiron (IS); Moshe Hayik, Hod Ha-Sharon (IS)

(*) Notice: Subject to any disclaimer, the term of this patent is extended or adjusted under 35 U.S.C. 154(b) by 0 days.

(21) Appl. No.: 16/284,080

(22) Filed: Feb. 25, 2019

(65) Prior Publication Data
US 2019/0290193 A1 Sep. 26, 2019

Related U.S. Application Data

(63) Continuation-in-part of application No. 15/934,960, filed on Mar. 24, 2018, now Pat. No. 10,722,710.

(51) Int. Cl.
*A61N 1/04* (2006.01)
*A61B 5/00* (2006.01)
A61M 16/06 (2006.01)
A61B 5/113 (2006.01)
A61B 5/1455 (2006.01)

(52) U.S. Cl.
CPC .......... *A61B 5/4818* (2013.01); *A61B 5/4809* (2013.01); *A61B 5/681* (2013.01); *A61N 1/0492* (2013.01); *A61B 5/113* (2013.01); *A61B 5/1455* (2013.01); *A61B 5/4815* (2013.01); *A61B 5/6823* (2013.01); *A61B 5/746* (2013.01); *A61M 16/06* (2013.01); *A61N 1/0452* (2013.01)

(58) Field of Classification Search
CPC ................ A61N 1/3625; A61N 1/3611; A61N 1/36014; A61N 1/0492; A61N 1/39044; A61B 5/4818
See application file for complete search history.

(56) References Cited

U.S. PATENT DOCUMENTS

| | | | |
|---|---|---|---|
| 2,711,729 A | 6/1955 | Hofmann | |
| 3,077,884 A | 2/1963 | Batrow et al. | |
| 4,827,935 A | 5/1989 | Geddes et al. | |
| 4,830,008 A | 5/1989 | Meer | |
| 5,348,008 A * | 9/1994 | Bornn | G16H 40/67 600/301 |
| 6,213,960 B1 * | 4/2001 | Sherman | A61N 1/39044 601/41 |
| 6,463,327 B1 | 10/2002 | Lurie et al. | |
| 6,587,726 B2 | 7/2003 | Lurie et al. | |
| 7,363,086 B1 | 4/2008 | Koh et al. | |
| 8,233,987 B2 | 7/2012 | Gelfand et al. | |
| 8,467,876 B2 | 6/2013 | Tehrani | |

(Continued)

Primary Examiner — Alyssa M Alter
(74) Attorney, Agent, or Firm — Barber Legal; Craig W. Barber

(57) ABSTRACT

A monitoring non-invasive device for handling of sleep apnea, snoring and emergency situations operates for breathing assistance by means of transdermal stimulation of muscle groups including the pectoralis majoris, the serratus anterior, and the abdominal muscles. A wrist mounted version may alarm drivers or others requiring focus or concentration when they fall asleep and may alert a medical center. The invention may have a pulse oximeter on a person's wrist/finger to monitor their breathing while asleep, and in the event of a serious snoring or sleep apnea episode, activate the breathing assistance pulses.

17 Claims, 22 Drawing Sheets

(56) References Cited

U.S. PATENT DOCUMENTS

| | | |
|---|---|---|
| 8,509,901 B2 | 8/2013 | Tehrani |
| 8,706,236 B2 | 4/2014 | Ignagni et al. |
| 8,934,977 B2 | 1/2015 | Errico et al. |
| 9,037,247 B2 | 5/2015 | Simon et al. |
| 9,375,571 B2 | 6/2016 | Errico et al. |
| 9,399,134 B2 | 7/2016 | Simon et al. |
| 9,555,260 B2 | 1/2017 | Simon et al. |
| 2003/0195571 A1 | 10/2003 | Burnes et al. |
| 2014/0163349 A1* | 6/2014 | Amitai .................. A61B 5/7203 600/393 |
| 2017/0027813 A1 | 2/2017 | Bobey et al. |

* cited by examiner

| | |
|---|---|
| TIME & DATE | 502 |
| MONITORING DATA, INHERENT | 504 |
| TYPE OF PULSE APPLIED | 506 |
| PULSE APPLIED DURATION | 508 |
| PULSE APPLIED FREQUENCY | 510 |
| PULSE APPLIED AMPLITUDE | 512 |
| MONITORING DATA, ASSISTED | 514 |

FIG. 8

NON-INVASIVE HANDLING OF SLEEP APNEA, SNORING AND EMERGENCY SITUATIONS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but reserves all copyright rights whatsoever. 37 CFR 1.71(d).

CROSS-REFERENCE TO RELATED APPLICATIONS

The present application claims the priority and benefit of previously filed U.S. Utility application Ser. No. 15/934,960 filed Mar. 24, 2018 in the name of the same inventors, Moshe Hayik and Ovadia Sagiv, and entitled, "Secretion Clearance and Cough Assist", the entirety of which is incorporated herein by this reference.

FIELD OF THE INVENTION

This invention relates generally to sleep apnea and snoring and assistance with breathing and specifically to non-invasive, non-implanted, non-mechanical, transdermal, monitored, automatic, sleep apnea, snoring, breathing, and ventilation assistance.

STATEMENT REGARDING FEDERALLY FUNDED RESEARCH

This invention was not made under contract with an agency of the US Government, nor by any agency of the US Government.

BACKGROUND OF THE INVENTION

Assisted breathing (which is different from mechanical breathing) is the attempt to help people suffering from Apnea (particularly sleep apnea), snoring, and other conditions causing momentary lack of breathing or weakened breathing. Those suffering sleep apnea may wake up more than 400 times in a single night, mostly without even realizing that their sleep has been disturbed.

Snoring is usually defined to be an unintended vocalization or noise during sleep caused by contractions in the various parts of the breathing system. Snoring by itself is linked to sleep deprivation, irritability, tiredness, and loss of momentary mental acuity. It is believed that it may in fact cause non-momentary psychological changes as well. Recent research suggests that there may even by a link (the carotid artery) between snoring and stroke. At this time there is no known cure for snoring, though some people are helped by surgery, weight loss or terminating smoking.

About 90 million Americans suffer from snoring activity during sleep. While half of these people are "simple snorers" or primary snorers, the other half may have the more serious condition of apnea or the forms of snoring which are pre-apnea. Due to the loss of sleep, which the sufferer may not even be aware of, sleep apnea sufferers are about 250% more likely to be involved in motor vehicle accidents.

Snoring can also be an early sign of obstructive sleep apnea. Sleep apnea is periods of actual, momentary, termination of breathing. Obstructive-type sleep apnea (which is between 80% and 90% of all sleep apnea) seems to relate to a relaxation of the walls of the throat and the tongue, allowing blockage. Sleep apnea has even worse effects on psychological well being than snoring, including judgement impairment, attention span degradation, memory issues, and so on. Untreated sleep apnea contributes to heart disease, high blood pressure, stroke, motor vehicle accidents, workplace problems and various other issues.

Snoring is the result of tissues in the throat relaxing enough that they partially block the airway and vibrate, creating sounds. Snoring is bothersome to those within earshot, but more importantly it may signal a more serious chronic condition known as obstructive sleep apnea, characterized by lapses in breathing or shallow breathing.

People with sleep apnea can stop breathing for greater than 10 seconds and do so over and over again due to this upper airway narrowing or collapse. FIG. 22 shows an example of this: the rear end of the tongue has relaxed backward into the throat, blocking it. The reduction in blood oxygen causes the heart to work harder.

The most significant effect of sleep apnea that the sleeper does not get a restful sleep, they may be sleepy during the day, which decreases their performance.

The present invention is directed toward long-term problems such as sleep apnea, but might be useful in therapy for short-term problems.

Breathing assistance, as used herein, refers to assisting the natural efforts of the body to breath. Various types of assistance are known, ranging from surgery to machinery.

The most common non-surgical solution to sleep apnea is the CPAP, a mechanical device with a face mask which is worn while asleep, using positive air pressure to force air into the lungs. Dental implants, surgery to the back of the tongue or throat and so on are also known. This therapy is awkward, due to requiring the constant usage of the face mask while asleep, but has been shown to reduce the incidence of motor vehicle accidents by up to 70% compared to untreated apnea sufferers.

Other known machines for assisting people with breathing are very large.

It would be preferable to provide a smaller, wearable machine, especially one small enough to be convenient for adults to allow complete comfort while asleep and a full range of activities when awake. (Note that sleep apnea is primarily a sleep problem and this invention is primarily concerned with sleep.) In addition, many types of machines rely upon electrodes implanted in the body and it would be preferable to provide a non-invasive machine which does not require surgery and surgical implants.

FIG. 1 is a PRIOR ART CPAP device, a mask worn over the face at night. It may apply differential pressure in order to force air into the user's airways. Note that this is not a solution conducive to normal sleep. Reference numerals on the PRIOR ART figures are not used in the present application and may be ignored.

FIG. 2 is a perspective view of a PRIOR ART dental plate. Again it may be seen that this is not a terribly easy or comfortable solution to the problem of sleep apnea.

FIG. 19 is a PRIOR ART device which at least uses a shirt, however, it also is not related to the present invention.

FIG. 20 is a PRIOR ART device which teaches that an electrode and a sensor may be combined into a single relatively smaller unit. This is useful, however, it does not specifically teach that a sufferer from sleep apnea may have stimulation to certain specific muscle groups not located in the airways.

A smaller and more recent apnea aid has been the nostril bridge which is fastened to the nostrils on the outside, with a mild adhesive, prior to sleep. This method also is not relevant to the present invention.

A newer ventilation method has been developed in recent decades for assisting with breathing, heart irregularities and so on. One example may be found in FIG. 3, which is a block diagram of a PRIOR ART implanted electrode method of stimulating nerves. Prior art implanted electrode 6 (there may be several or just one) is implanted in the chest: it may be subdermal, or deep inside the thoracic cavity, it may be implanted to stimulate the heart or other muscles or it may be placed quite close to the phrenic nerve 8. The phrenic nerve 8 is frequently mentioned as being stimulated in prior art.

Note that other implanted electrode devices may stimulate the diaphragm muscle so as to assist with breathing/ventilation. However, the present invention does not deal with implanting devices.

Obviously implanting electrodes is very undesirable. Not only is a surgery required but the electrode is a foreign object in the body, with all the potential issues which may arise from that. The electrode cannot be easily checked or replaced, may degrade, and may be psychologically unwelcome to the person.

Finally, although the phrenic nerve has proven to be a useful target for stimulation, it would be preferable to provide easier and more effective targets for stimulation.

It would be preferable to provide targets for breathing assistance, apnea assistance and snoring assistance which require no electrodes to be implanted at all.

It would also be preferable to provide a device and method of ventilation assistance which monitors the wearer for a momentary lack of breathing, weakened breathing, or serious sleep snoring and in the event of serious sleep apnea or serious snoring disorder, automatically begins treatment of ventilation until recovery, while in parallel logging the event in a control device interface (such as a smart phone) and furthermore sending a note of the event to a medical center.

It would further be preferable to provide a device and method of ventilation assistance which does not require or force the person to breath but rather relies up on the body's own breath reflex, assisting that natural autonomic breathing rather than replacing it.

It would further be preferable to provide convenient control mechanisms so that not just medical professionals but persons themselves can monitor breathing, apnea, snoring and other information and control it as necessary and practical.

It would further be preferable to provide a device and method which leaves the person with a complete range of motion including mobility, uses small batteries, and allows essentially all normal activities.

It would further be preferable to provide a device and method which requires no face mask, no hoses, tubes or implanted electrodes. It would be preferable to provide a method which is fully electronic and yet requires no implantation or other surgery.

It would further be preferable to provide a device with a simple wrist, or finger mounted monitor such as a pulse oximeter or the like.

It would further be preferable to provide a device and method which operates by means of multiple different actions: small contractions, larger muscle stimulations, options of different musculature usage and so on. Note that a diaphragm or heart stimulation technique by way of an implanted electrode has only a single choice of target, but the present invention is not so limited.

These and other aspects and objectives are addressed by the present invention.

SUMMARY OF THE INVENTION

General Summary

The present invention teaches a device which operates for snoring compensation, sleep apnea support, emergency situations, and breath assistance by monitoring breathing and automatic application of transdermal stimulation of certain muscle groups involved in breathing. (However the diaphragm muscle is not presently implicated.) Muscles used in various phases include the pectoralis majoris, the serratus anterior, and the abdominal muscles. These are stimulated by pulse trains applied from electrode patches on the surface of the skin, without need for any implantation procedure at all.

It may be seen that the abdominal muscles come in various pairs or groups and that different combinations may be used depending on circumstances, efficiency and so forth. The same choices are allowed for the muscles of the chest when they are stimulated. Finally, the various muscle groups may be stimulated in different ways: not just different pulse trains but in addition, different stimulations to accomplish different phases of ventilation assistance.

The present invention teaches that the device of the invention may have a monitor and a stimulator, as well as transdermal electrodes attached to the skin of the user. The invention does not force breathing but rather assists breathing by the wearer.

The monitor may be a pulse oximeter or other monitor of breathing, pulse, oxygen content and so on. It may beneficially be attached to the wrist, finger, hand, etc, in the form of a wearable band, a ring, bracelet, sticker or the like, or in alternative embodiments the torso for other types of monitoring. There are known methods of using iPhone® apps to measure heart parameters, these methods are not entirely well researched at the present time but if found to be reliable, then more stylish monitors may hypothetically be incorporated within the present invention.

Beneficially, the invention might even be used to supplement natural breathing action: for example in one alternative, the device of the invention may await a natural breath reflex detection and then promptly aid the action of the torso muscles so that a more efficient breathing is attained.

In addition, the present invention teaches that a driver who is being stimulated for assisted breathing may be alerted, by means of an audible/vibration/transmitted signal from the wrist/finger monitor unit, or an audible/vibration/transmitted signal from a control module, or a mobile device such as a tablet or phone. For this application, the word driver is defined to be "a person in a job requiring attention and focus", and in fact anyone in any job requiring attention and focus, such as pilots, truck drivers, bus drivers, but also including life guards, prison guards, medical professionals, air traffic controllers, and so on.

In addition, at the time a driver is being stimulated, the device may also communicate, for example via a communication protocol such as V2X, with an autonomous or semi-autonomous vehicle which the driver is driving. The alert may in fact direct the vehicle to apply brakes, or activate emergency/distress lights, or begin autonomous driving, with instructions such as to return to the driver's home, pull over at the next safe place to park the vehicle, return to a preprogrammed location or the like.

The disclosed method and system for assistance in managing snoring, apnea and ventilation is in fact fully electronic with no mechanical or pneumatic part, and yet is highly effective at ventilation.

Yet it is also non invasive—there is no need for surgery and no need to simulate the spinal cord tracts. Furthermore it is silent and very energy efficient—can work using a small battery for a week and more.

The method and device is comprised of a special wearable part with electrodes and control module that generate special patterns of signals (according to desired algorithms) which signals are sent to the electrodes. The device thus electrically transdermally stimulates directly the pectoralis major and serratus anterior muscles and the abdominal muscles for breathing assistance.

The control module has a start button to start operations with present parameters, and includes wireless communication to a smart phone for display of data, results, and so on, not to mention allowing wireless setup, maintenance and control The control module may optionally include a small touch screen display for setup of the parameters and display of the results.

Preliminary Notes:

Muscle Physiology and the response to electronic stimulation:

The muscle responds to a single electronic stimulation with a quick contraction and relaxation. The stimulus that results in a muscle twitch is based on the magnitude of the stimulus (voltage) and the rate at which stimuli are applied (frequency).

Magnitude of Electric Stimulation:

The strength of the twitch increases with the increase in the magnitude of the shock. Therefore, the strength of the twitch is said to be graded (or incrementally increased). This is due to the recruitment of increased numbers of muscle fibers that are involved in the twitch. Thus, an electronically assisted breath of air can in fact be physically stronger than an unassisted breath, and yet the augmentation or strengthening is entirely due to physical muscle action only.

Frequency of Electric Stimulation:

If the frequency of the shock is increased, the second stimulus will be applied before the first muscle twitch is over, then the second stimulus will build upon the previous contraction and add to that response. If the frequency will be increased more, eventually no relaxation will be allowed and the muscle contraction will increase smoothly up to a point of maximum strength.

Summary in Reference to Claims

It is therefore another aspect, advantage, objective and embodiment of the invention, in addition to those discussed previously, to provide a sleep apnea, snoring, emergency situations and breath assistance device for use by a person having a body, and an arm, such arm having a wrist, a hand, and fingers, the person engaged in autonomic breath, the sleep apnea, snoring, emergency situations and breath assistance device comprising:

a device body having a shape dimensioned and configured to be worn on such arm;

a control module including a CPU within the device body;

a first electrode in contact with such arm, the control module having operative electrical connections to the first electrode;

an RF communication module;

at least one sensor of at least one physiological parameter;

the control module further comprising an analysis module operative to receive data from the sensor and analyze the data to determine if such person is exhibiting such autonomic breath and if such person is not exhibiting such autonomic breath for a period of 3 seconds, the control module further operative to carry out one task selected from the group consisting of: send a first pulse train to the first electrode, communicate via the RF communication module, communicate via the RF communication module with a vehicle, and combinations thereof.

It is therefore another aspect, advantage, objective and embodiment of the invention, in addition to those discussed previously, to provide a sleep apnea, snoring, emergency situations and breath assistance device for use by a person having a body, and an arm, such arm having a wrist, a hand, and fingers, the person engaged in autonomic breath, the sleep apnea, snoring, emergency situations and breath assistance device comprising:

a device body having a shape dimensioned and configured to be worn on such arm;

a control module including a CPU within the device body;

a first electrode in contact with such arm, the control module having operative electrical connections to the first electrode;

an RF communication module;

at least one sensor of at least one physiological parameter;

the control module further comprising an analysis module operative to receive data from the sensor and analyze the data to determine if such person is exhibiting such autonomic breath and if such person is not exhibiting such autonomic breath, the control module further operative to carry out one task selected from the group consisting of: send a first pulse train to the first electrode, make an alert noise, make an alert vibration, communicate via the RF communication module, communicate via the RF communication module with a vehicle, communicate via the RF communication module with a first preferred remote terminal, and combinations thereof.

It is therefore another aspect, advantage, objective and embodiment of the invention, in addition to those discussed previously, to provide a sleep apnea, snoring, emergency situations and breath assistance device for use by a person having a body, skin, a mouth, airways, first, second, third, and fourth pairs of abdominal muscles, and chest muscles including pectoral muscles and serratus anterior muscles, the sleep apnea, snoring, emergency situations and breath assistance device comprising:

a control module having operative electrical connections to a plurality of dermal electrodes attached to such skin of such person, the control module small enough to be worn on such person body;

a first one of the dermal electrodes disposed on such skin of such person at one such chest muscle;

a second one of the dermal electrodes disposed on such skin of such person at one such abdominal muscle;

the control module having a stimulation module operative to send a first pulse train to such chest muscle and a second pulse train to such abdominal muscle;

the first pulse train operative to stimulate such chest muscle so as to cause a first contraction of such chest muscle;

the second pulse train operative to stimulate such abdominal muscle so as to cause a second contract of such abdominal muscle;

whereby at least one breath is stimulated.

It is therefore another aspect, advantage, objective and embodiment of the invention, in addition to those discussed previously, to provide a sleep apnea, snoring, emergency situations and breath assistance device for use with a first garment worn on such body by such person, wherein:

the control module, the dermal electrodes and the operative electrical connections are small enough to be worn on such body concealed within such first garment, and further comprising:

a second garment worn about such body by such person, the second garment concealed within such first garment, and the second garment concealing the control module, dermal electrodes and operative electrical connections within itself.

It is therefore another aspect, advantage, objective and embodiment of the invention, in addition to those discussed previously, to provide a sleep apnea, snoring, emergency situations and breath assistance device further comprising:
a third one of the dermal electrodes disposed on such skin of such person at a second such abdominal muscle;
a fourth one of the dermal electrodes disposed on such skin of such person at a third such abdominal muscle;
a fifth one of the dermal electrodes disposed on such skin of such person at a fourth such abdominal muscle;
the control module further operative to send the second pulse train to such second, third and fourth abdominal muscles.

It is therefore another aspect, advantage, objective and embodiment of the invention, in addition to those discussed previously, to provide a sleep apnea, snoring, emergency situations and breath assistance device further comprising:
a sixth one of the dermal electrodes disposed on such skin of such person at a second such chest muscle;
a seventh one of the dermal electrodes disposed on such skin of such person at a third such chest muscle;
an eighth one of the dermal electrodes disposed on such skin of such person at a fourth such chest muscle;
the control module further operative to send the first pulse train to such second, third and fourth chest muscles.

It is therefore another aspect, advantage, objective and embodiment of the invention, in addition to those discussed previously, to provide a sleep apnea, snoring, emergency situations and breath assistance device wherein the pulse train further comprises:

a group of pulses consisting of a plurality of individual pulses increasing in amplitude with time, the group of pulses having a duration of 500 ms to 900 ms;
a second time out period of 2 to 3 seconds during which no pulses are sent;
repetitions of the group of pulses and the second time out period for a breath assist time period defined to last either until an autonomic breath occurs or for a period of time of no more than 3 seconds.

It is therefore another aspect, advantage, objective and embodiment of the invention, in addition to those discussed previously, to provide a sleep apnea, snoring, emergency situations and breath assistance device further comprising:
at least one sensor of at least one physiological parameter;
the at least one sensor being a pulse oximeter attached to such user;
the pulse oximeter sensor in operative communication with the control module;
the control module further comprising an analysis module operative to receive a data from the pulse oximeter sensor and analyze the data to determine if such person is exhibiting an autonomic breath and if such person is not exhibiting an autonomic breath for a period of 3 seconds, the control module further operative to send the pulse trains.

It is therefore another aspect, advantage, objective and embodiment of the invention, in addition to those discussed previously, to provide a sleep apnea, snoring, emergency situations and breath assistance device further comprising:

at least one sensor of at least one physiological parameter;
the at least one sensor being a breath sensor, the breath sensor in operative communication with the control module, the breath sensor disposed on such skin of such person; the control module further comprising an analysis module operative to receive a data from the breath sensor and analyze the data to determine if such person is exhibiting an autonomic breath and if such person is not exhibiting an autonomic breath for a period of 3 seconds, the control module further operative to send the pulse trains.

It is therefore another aspect, advantage, objective and embodiment of the invention, in addition to those discussed previously, to provide a sleep apnea, snoring, emergency situations and breath assistance device further comprising:
at least one sensor of at least one physiological parameter;
the at least one sensor being a blood oxygen level sensor, the blood oxygen level sensor in operative communication with the control module, the blood oxygen level sensor disposed on such skin of such person;
the control module further comprising an analysis module operative to receive a data from the blood oxygen level sensor and analyze the data to determine if such person is exhibiting an oxygen level indicative of a normal breathing pattern and if such person is not, the control module further operative to send the pulse trains.

It is therefore another aspect, advantage, objective and embodiment of the invention, in addition to those discussed previously, to provide a sleep apnea, snoring, emergency situations and breath assistance device, further comprising:
at least one sensor of at least one physiological parameter;
the at least one sensor being a blood pressure sensor, the blood pressure sensor in operative communication with the control module, the blood pressure sensor disposed on such skin of such person;
the control module further comprising an analysis module operative to receive a data from the blood pressure sensor and analyze the data to determine if such person is exhibiting normal autonomic breathing and if such person is not exhibiting normal autonomic breathing, the control module further operative to send the pulse trains.

It is therefore another aspect, advantage, objective and embodiment of the invention, in addition to those discussed previously, to provide a sleep apnea, snoring, emergency situations and breath assistance device, further comprising:
at least one sensor of at least one physiological parameter;
the at least one sensor being a heart rate sensor, the blood pressure sensor in operative communication with the control module, the heart rate sensor disposed on such skin of such person;
the control module further comprising an analysis module operative to receive a data from the heart rate sensor and analyze the data to determine if such person is exhibiting normal autonomic breathing and if such person is not exhibiting normal autonomic breathing, the control module further operative to send the pulse trains.

It is therefore another aspect, advantage, objective and embodiment of the invention, in addition to those discussed previously, to provide a sleep apnea, snoring, emergency situations and breath assistance device, further comprising:
an RF communication module;
a mobile device having an operative RF connection to the RF communication module of the control module;
the mobile device having a module operative to provide wireless control of the operation of the control module;
the mobile device operative to collect data, provide for wireless setup and wireless maintenance of the sleep apnea, snoring, emergency situations and breath assistance device.

It is therefore another aspect, advantage, objective and embodiment of the invention, in addition to those discussed previously, to provide a sleep apnea, snoring, emergency situations and breath assistance device, further comprising:

the control module having a non-volatile memory and a central processor unit, the analysis module stored in the non-volatile memory.

It is therefore another aspect, advantage, objective and embodiment of the invention, in addition to those discussed previously, to provide a sleep apnea, snoring, emergency situations and breath assistance device, wherein the control module further comprises:

a touch screen operative to display a set of data collected by the sleep apnea, snoring, emergency situations and breath assistance device and enable control of the sleep apnea, snoring, emergency situations and breath assistance device.

It is therefore another aspect, advantage, objective and embodiment of the invention, in addition to those discussed previously, to provide a sleep apnea, snoring, emergency situations and breath assistance device, wherein the control module has a start button operative to activate the sleep apnea, snoring, emergency situations and breath assistance device to begin an operating cycle, using a first set of preset operating parameters stored in the non-volatile memory;

the start button further operative to establish the operative RF connection to the mobile device.

It is therefore another aspect, advantage, objective and embodiment of the invention, in addition to those discussed previously, to provide a sleep apnea, snoring, emergency situations and breath assistance device, wherein the mobile device is operative to provide control of the control module by one mode selected from the group consisting of: manual control input to the mobile device and the control module, manual control input to the mobile device and from the mobile device to the control module, adaptive heuristic control by an artificial intelligence module loaded in the mobile device and the control module, adaptive heuristic control by an artificial intelligence module loaded in the mobile device and from the mobile device to the control module, remote control from a remote location via communication with the mobile device and from the mobile device to the control module, and combinations thereof.

It is therefore another aspect, advantage, objective and embodiment of the invention, in addition to those discussed previously, to provide a sleep apnea, snoring, emergency situations and breath assistance device, wherein the pulse oximeter sensor is further operative to alert such person by means of an audible/vibration/transmitted signal when it sends such pulse trains.

It is therefore another aspect, advantage, objective and embodiment of the invention, in addition to those discussed previously, to provide a sleep apnea, snoring, emergency situations and breath assistance device, wherein the control module is further operative to alert such person by means of an audible/vibration/transmitted signal from such mobile device when it sends such pulse trains.

It is therefore another aspect, advantage, objective and embodiment of the invention, in addition to those discussed previously, to provide a sleep apnea, snoring, emergency situations and breath assistance device, wherein the communication protocol further comprises one member selected from the group consisting of: V2X, Bluetooth, WiFi, and combinations thereof.

It is therefore another aspect, advantage, objective and embodiment of the invention, in addition to those discussed previously, to provide a sleep apnea, snoring, emergency situations and breath assistance device, for use by such person in a job requiring attention and focus.

It is therefore another aspect, advantage, objective and embodiment of the invention, in addition to those discussed previously, to provide a sleep apnea, snoring, emergency situations and breath assistance device, for use with a vehicle being driven by such person, such vehicle having autonomous driving capability, wherein the control module further comprises:

a communication protocol allowing the control module to control such vehicle;

the control module operative to assume control of such vehicle when it sends such pulse trains.

It is therefore another aspect, advantage, objective and embodiment of the invention, in addition to those discussed previously, to provide a sleep apnea, snoring, emergency situations and breath assistance device, wherein the communication protocol further comprises: V2X.

It is therefore another aspect, advantage, objective and embodiment of the invention, in addition to those discussed previously, to provide a method of breath assistance for use by a person having skin, a mouth, airways, first, second, third, and fourth pairs of abdominal muscles, and chest muscles including pectoral muscles and serratus anterior muscles, the breath assistance method comprising the steps of:

sending a first pulse train controlled by a first set of parameters to a first electrode disposed on such skin of such person at one such chest muscle, the first pulse train operative to stimulate such chest muscle so as to cause a first contraction of such chest muscle;

sending a second pulse train to a second electrode disposed on such skin of such person at a first such abdominal muscle, the second pulse train operative to stimulate such abdominal muscle so as to cause a first contraction of such abdominal muscle;

whereby at least one assisted breath is stimulated.

It is therefore another aspect, advantage, objective and embodiment of the invention, in addition to those discussed previously, to provide a method of breath assistance further comprising:

monitoring such person and sending a data set to an analysis module;

determining by means of the analysis module when such person is exhibiting an autonomic breath and when such person is exhibiting an autonomic breath, sending the first pulse train.

It is therefore another aspect, advantage, objective and embodiment of the invention, in addition to those discussed previously, to provide a method of breath assistance further comprising:

wirelessly accessing the analysis module from a remote location; and providing the data set to the remote location.

It is therefore another aspect, advantage, objective and embodiment of the invention, in addition to those discussed previously, to provide a method of breath assistance further comprising:

wirelessly altering the first set of parameters from the remote location.

It is therefore another aspect, advantage, objective and embodiment of the invention, in addition to those discussed previously, to provide a sleep apnea, snoring, emergency situations and breath assistance device, for use by a person having a body, skin, a mouth, airways, first, second, third, and fourth pairs of abdominal muscles, and chest muscles including pectoral muscles and serratus anterior muscles, the sleep apnea, snoring, emergency situations and breath assistance device comprising:

a control module having operative electrical connections to a plurality of zone group stimulators attached to such skin of such person, the control module small enough to be worn on such person body;

a first one of the zone group stimulators disposed on such skin of such person at at least one such chest muscle;

a second one of the zone group stimulators disposed on such skin of such person at at least one such abdominal muscle;

the control module having a stimulation module operative to send a first pulse train to such chest muscle and a second pulse train to such abdominal muscle;

the first pulse train operative to stimulate such chest muscle so as to cause a first contraction of such chest muscle, the contraction of such chest muscle thereby causing a second contraction of such airways;

the second pulse train operative to stimulate such abdominal muscle so as to stimulate at least one breath.

It is therefore another aspect, advantage, objective and embodiment of the invention, in addition to those discussed previously, to provide a sleep apnea, snoring, emergency situations and breath assistance device, further comprising:

a pulse train further comprising:

a group of pulses consisting of a plurality of individual pulses increasing in amplitude with time, the group of pulses having a duration of 500 ms to 900 ms;

a second time out period of 2 to 3 seconds during which no pulses are sent;

repetitions of the group of pulses and the second time out period for a breath assist time period defined to last either until an autonomic breath occurs or for a period of time of no more than 3 seconds.

BRIEF DESCRIPTION OF THE DRAWINGS

FIG. 8 is a simple data structure as might be used by the device to assist therapeutic activities, to test the device or to optimize usage of the device for a given person or condition.

FIG. 9 is a transparent frontal view of a person wearing the present invention device, showing the device worn inside of an ordinary garment such as a t-shirt, and with a wrist monitor of a larger type able to accurately measure blood pressure as well as breathing, pulse, oxygen levels and the like.

FIG. 16 is a transparent frontal view of a person wearing an embodiment of the present invention device, showing the device worn inside of an ordinary garment such as a t-shirt, and with a wrist monitor of a larger type able to accurately measure blood pressure as well as breathing, pulse, oxygen levels and the like.

INDEX TO REFERENCE NUMERALS

Figure 1:
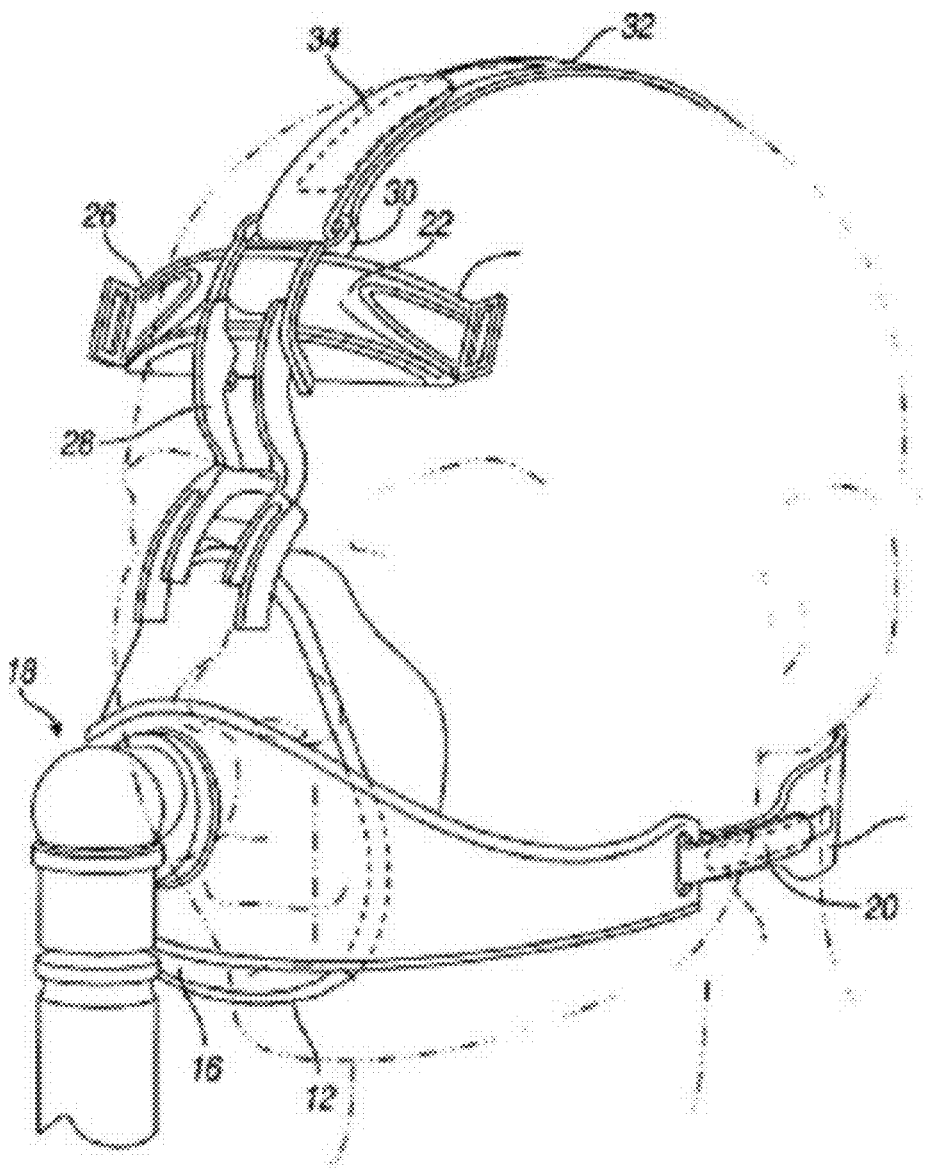
FIG. 1 is a perspective view of PRIOR ART, a CPAP mask for night-time use.

Prior art implanted electrode 6
Phrenic nerve stimulated in prior art 8
Person 100
System 102
Pectoralis major 104
Serratus anterior 106
Abdominal muscles 108
Dermal electrode pads 110
Leads 112
Control module 114
RF connection (Bluetooth®, Wifi, etc) 116
Mobile device (smart phone) 118
Autonomic breathing detector 120
Monitor parameters 202
Breathing assist required? 204
Begin assistance 206
Monitor assisted breathing 208
Breathing returns to normal? 210
Alert medical center 212
Send event log to medical center 214

Exemplary pulse trains 302, 304, 306, 308
System 400
Operating system 402
Power management 404
Controller unit 406
Memory 410
Processor (CPU) 412
Optional display screen control 414
Breathing monitor 416
Analysis module 418
Stimulation control module 420
RF communication (ex. Bluetooth®/Wifi) 422
Mobile device 424
Control module 426
App display module 428
App user input control module 430
User history module 432
Help module 434
Event 500
Time&Date 502
Autonomic breath monitored data 504
Pulse train stimulation applied type 506
Pulse train stimulation applied duration 508
Pulse train stimulation applied frequency 510
Pulse train stimulation applied amplitude 512
Assisted breathing monitored data 514
Garment 900
Dermal electrode pads 910
Leads 912
Control module 914
Torso monitor 920
Wrist/finger monitor/pulse oximeter 950
Person 1200
System 1202
Control module/mobile device 1214
Garment 1360
Person 1400
Electrical lead 1412
Control module 1414
Sensor/monitor 1420
Zone "A" (pectoralis) stimulator pad 1472
Zone "B" (serratus) stimulator pad 1474
Zones "C" and "D" (abdominal) stimulators 1476
Person 1500
Pectoralis major 1504
Serratus anterior
Abdominal muscles 1508
Dermal zone stimulation pads 1510
Leads 1512
Control module 1514
RF connection (Bluetooth®) 1516
Mobile device (smart phone) 1518
Breath detector/monitor 1520
Person 1600
Dermal stimulation pad 1610
Electrical lead 1612
Control module 1614
Sensor/combination sensor & electrode 1620
Wrist monitor unit 1650
Person 1700
Electrical lead 1712
Control module 1714
Sensor/stimulator 1720
Zone "A" (pectoralis) stimulator pad 1772
Zone "B" (serratus) stimulator pad 1774
Zones "C" and "D" (abdominal) stimulators 1776
Safety device 1800

Bio sensor 1802
CPU 1804
LCD/OLED display 1806
Electrode, internal 1808
Memory 1810
V2X/RF communication 1812
Bluetooth/Wifi/RF communication 1814
Power supply/battery 1816
Autonomous/semi-autonomous vehicle 1818
Control module 1820
Mobile phone/mobile device 1822

DETAILED DESCRIPTION

Glossary

For this application, the word driver is defined to be "a person in a job requiring attention and focus", and in fact anyone in any job requiring attention and focus, such as pilots, truck drivers, bus drivers, but also including life guards, prison guards, medical professionals, air traffic controllers, and so on.

As used herein the words breath and breathe carry their ordinary meanings. An autonomic breath however refers to a breath which occurs naturally, due to normal internal processes such as build up of $CO_2$. This is distinguished from breaths which may be deliberately initiated by the user of the invention or even (possibly) be triggered by the invention. Promoting a breath refers to either or both of a) increasing the power of an autonomic breath by detecting it and applying electrical stimulation to abdominal muscles so as to increase the number of muscle fiber bundles which contribute force to the breath, (also called herein an "assisted breath", and/or b) causing a breath deliberately by means of the invention.

Skin, mouth, throat, abdominal muscles, and chest muscles including pectoral muscles and serratus anterior muscles all have their ordinary meanings Note that all such muscles may be stimulated transdermally ("through the skin") by placement of a dermal ("on the skin") electrode which electrode does NOT itself need to be implanted in the skin. Such electrodes may be attached by adhesives designed to hold well to human skin and yet promote electrical transmission between electrode and skin.

As used herein "airways" refers to the respiratory system passages which allow air to enter and leave the human body, including, but not limited to, the trachea, bronchus, bronchi, bronchiole, alveoli, as well as to anatomical features which allow air flow like the muscles around these airways and so on and so forth.

As used in the claims attached herein, the word "such" indicates parts or aspects of a human person and are pre-ambular language.

The present invention teaches zone stimulator pads which cover a substantial part of a muscle group: a zone electrode may have one, or preferably more than one large enough electrode(s) within it as an inner layer. The large electrodes within the zone electrode may be in direct touching contact with the skin and be inside of a large fabric enclosure. The fabric forms a second layer on the outside of the electrodes, insulating the electrodes (the fabric has insulating properties) from contact with garments, other body parts, etc.

The zone stimulators of the invention may in fact stimulate a "group" of muscles, or a large muscle over a considerable area of the muscle rather than a single point (thus acting like a group of electrodes) and thus the term "zone group stimulators" is also used interchangeably with the term zone stimulators.

Stimulation or stimulating may refer either to causing a breath or assisting an autonomic breath already in progress.

There are two possible categories of garments in the present document. Outer garments or "the first garment" may be an ordinary garment such as a shirt, wrap, blouse, sweater or the like, which may cover or conceal the invention in embodiments located on the torso, but which is essentially not part of the invention. A "second garment" on the other hand is a garment which is specifically designed to be part of the invention, usually a smaller garment such as a wrap, sash, harness or the like which is itself concealed within the "first garment".

As used herein a "signal" may be an audible/vibration/transmitted signal, such as a tone or beep, music, or a vibration, or may be a signal transmitted to another device such as a mobile device or control unit or vehicle, which then alerts the user or a medical professional.

End Glossary

Figure 2:
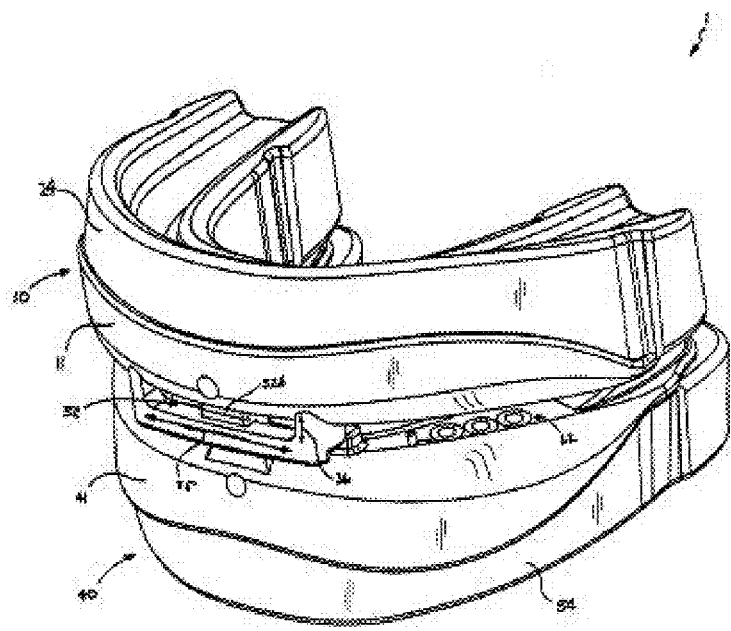
FIG. 2 is a perspective view of PRIOR ART dental device for sleep apnea.
Figure 3:
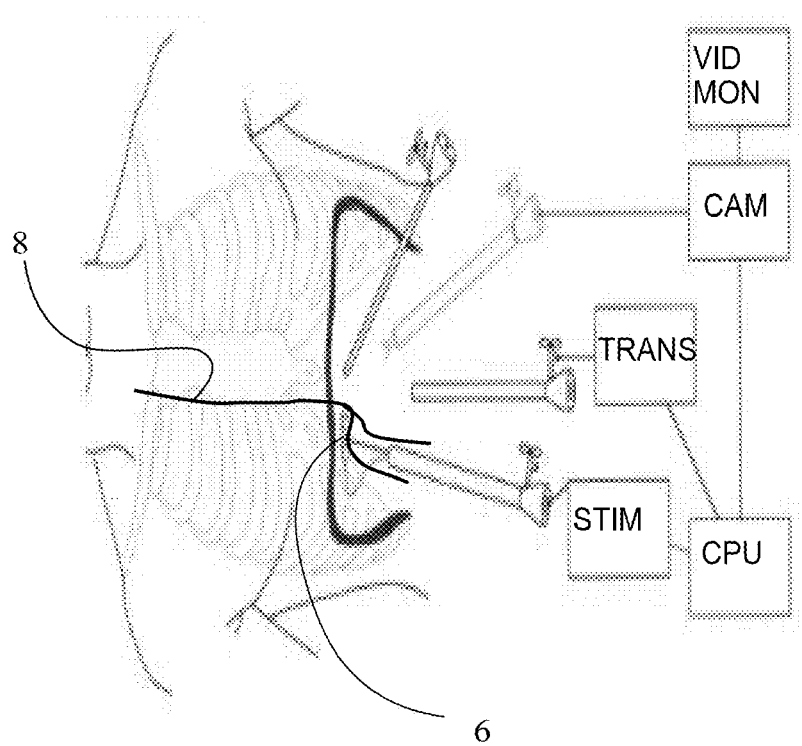
FIG. 3 is a block diagram of a PRIOR ART implanted electrode method of stimulating the phrenic nerve.

FIG. 1 is a perspective view of a PRIOR ART CPAP method of assisting breathing, while FIG. 2 is a perspective view of a PRIOR ART dental device and FIG. 3 is a block diagram of a PRIOR ART implanted electrode method of stimulating the phrenic nerve, all as discussed previously in the BACKGROUND section of the present application.

Figure 19:
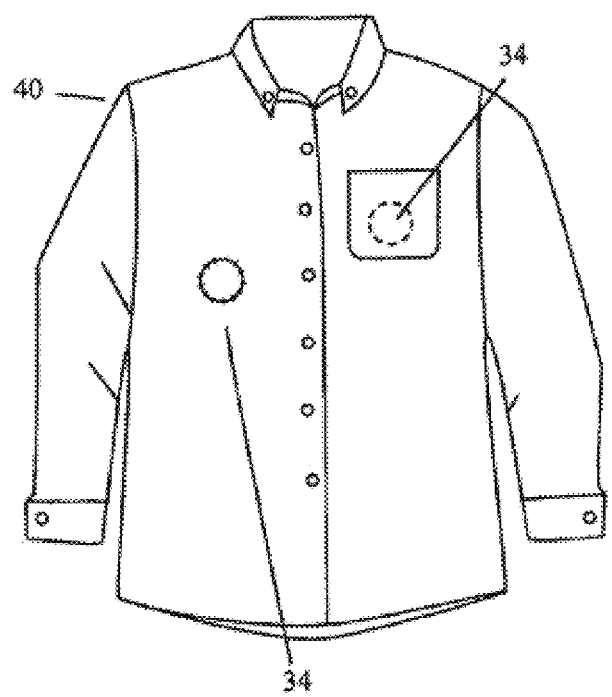
FIG. 19 is a perspective view of PRIOR ART wearable in a shirt.
Figure 20:
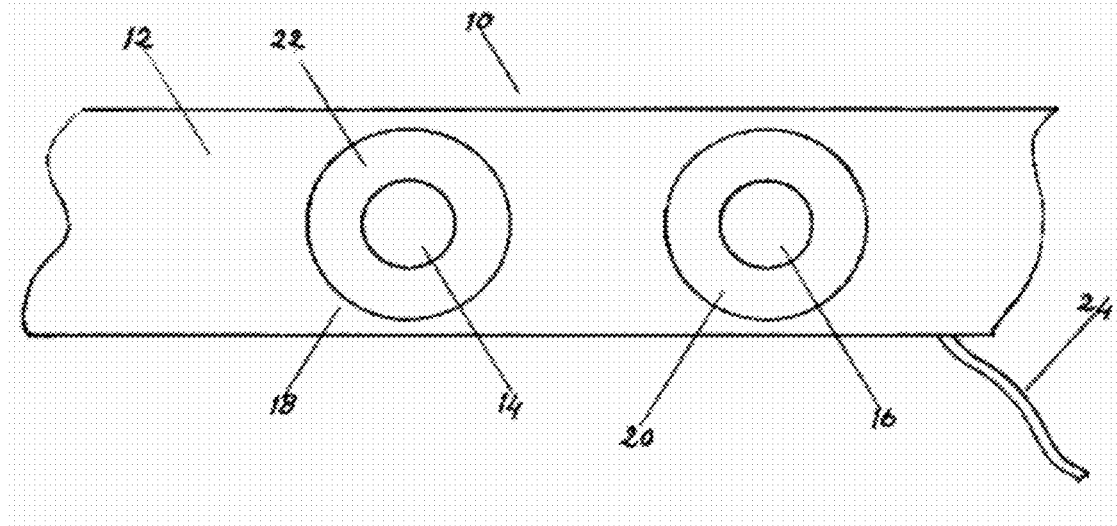
FIG. 20 is a perspective view of PRIOR ART stimulation pads on a band for transdermal stimulation.

FIG. 19 is a PRIOR ART drawing showing another device showing transdermal stimulation for breathing assistance which is usable underneath a shirt, while FIG. 20 is a PRIOR ART drawing showing a band and pair of stimulators.

Figure 4:
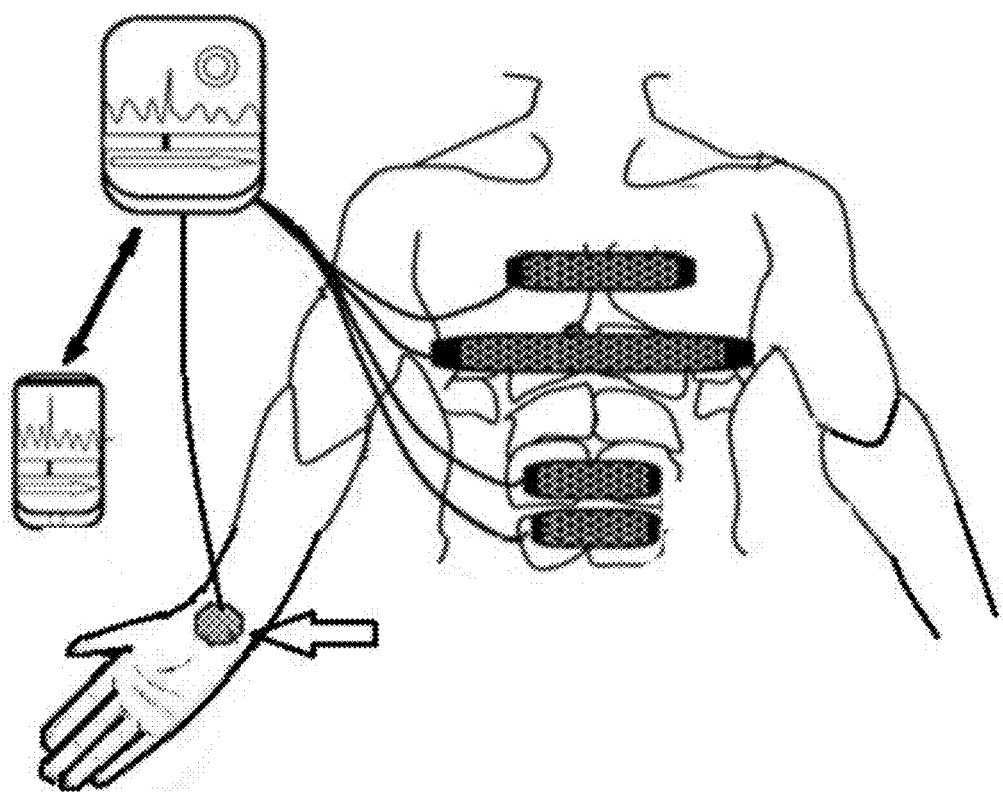
FIG. 4 is an overview block diagram of the first embodiment of the present invention showing relevant muscle groups, lack of implants, dermal electrodes and sensors, the control module and a mobile device which serves as control and input/output for the device.

FIG. 4 is an overview block diagram of the first embodiment of the present invention showing relevant muscle groups, lack of implants, dermal electrodes and sensors, the control module and a mobile device which serves as control and input/output for the device.

Person 100 is attached to system 102 by leads 112 to dermal electrode pads 110, which are placed on the surface of the person's skin.

The location of the dermal electrode pads is important, as the dermal electrode pads 110 will be used to transmit signals through the skin (transdermally) to the underlying muscles. Thus pads which are properly placed over the muscles of interest will activate the desired muscles. Two pads are shown located on the pectoralis major 104 muscles of the upper front chest, while two more pads are shown over the serratus anterior 106 chest muscles (note that in a two dimensional diagram it may be hard to see the three dimensional layout of the musculature).

The chest muscles tend to be implicated in breathing, that is, to draw breath a human autonomic system with expand the diaphragm downward and the chest muscles outward, while to exhale the automatic reflex is to compress the chest muscles inward and squeeze the diaphragm upward into the chest cavity. In this case however, the diaphragm is not shown and the phrenic nerve is not shown as they are totally uninvolved in the present invention, which teaches an alternative to their usage. The chest muscles are shown, and the present invention utilizes them of inhalation and exhalation, another unique aspect of the invention.

Finally, abdominal muscles 108 may all have, or some may have dermal electrode pads 110 as well. There are a large number of abdominal muscles, these are implicated in breathing action.

The present invention teaches that electrodes may be placed over the chest muscles (in particular the pectoralis and serratus discussed above) to activate these muscles, for breathing.

The abdominal muscles are stimulated as well, to promote breathing. As noted previously, "promote" in this application means either causing an artificially induced breath, or, by activating musculature (in particular muscle bundles) while an autonomic ("natural") breath is occurring, it increases the number of muscle fiber bundles available and used in the breath, thus increasing the power of the breath.

In use in a preferred embodiment and best mode presently contemplated, one or more breaths are induced. In a second and also preferred embodiment and best mode presently contemplated, instead of inducing artificial breaths, the system awaits an autonomic breath and then stimulates the abdominal muscles to promote the autonomic breath by strengthening it. In alternative embodiments, it may be found efficient to have the stimulation happen concurrently with the breathing or perhaps even after, or there may be multiple rounds of stimulation for each breath, and so on.

Leads 112 lead to control module 114. Control module 114 will be discussed further in reference to FIG. 7, but in summary has a number of modules or physical machines which are able to control the activation of the electrodes and cause mild electrical charges to be applied thereby.

RF connection (such as Bluetooth®, Wifi, or other equivalents) 116 in turn connects the control module 114 to a mobile device 118, which may be a smart phone, an iPhone, an Android phone, or it may be a tablet or music player or pod, a tablet PC, a laptop or netbook or other similar device. The mobile device 118 has a "control module" (meaning a programmed function) which controls the "control module" (114, meaning the hardware device connected to and controlling the electrodes).

Finally autonomic breath detector 120 may optionally be employed to detect autonomic breaths (that is breaths which the body generates without artificial stimulation), and it may also be used to monitor breathing, to monitor the efficiency of different types, frequencies, amplitudes and wave forms of stimulation, and transmit data collected on person breaths, breathing, and so on, to the control module 114.

Figure 5:
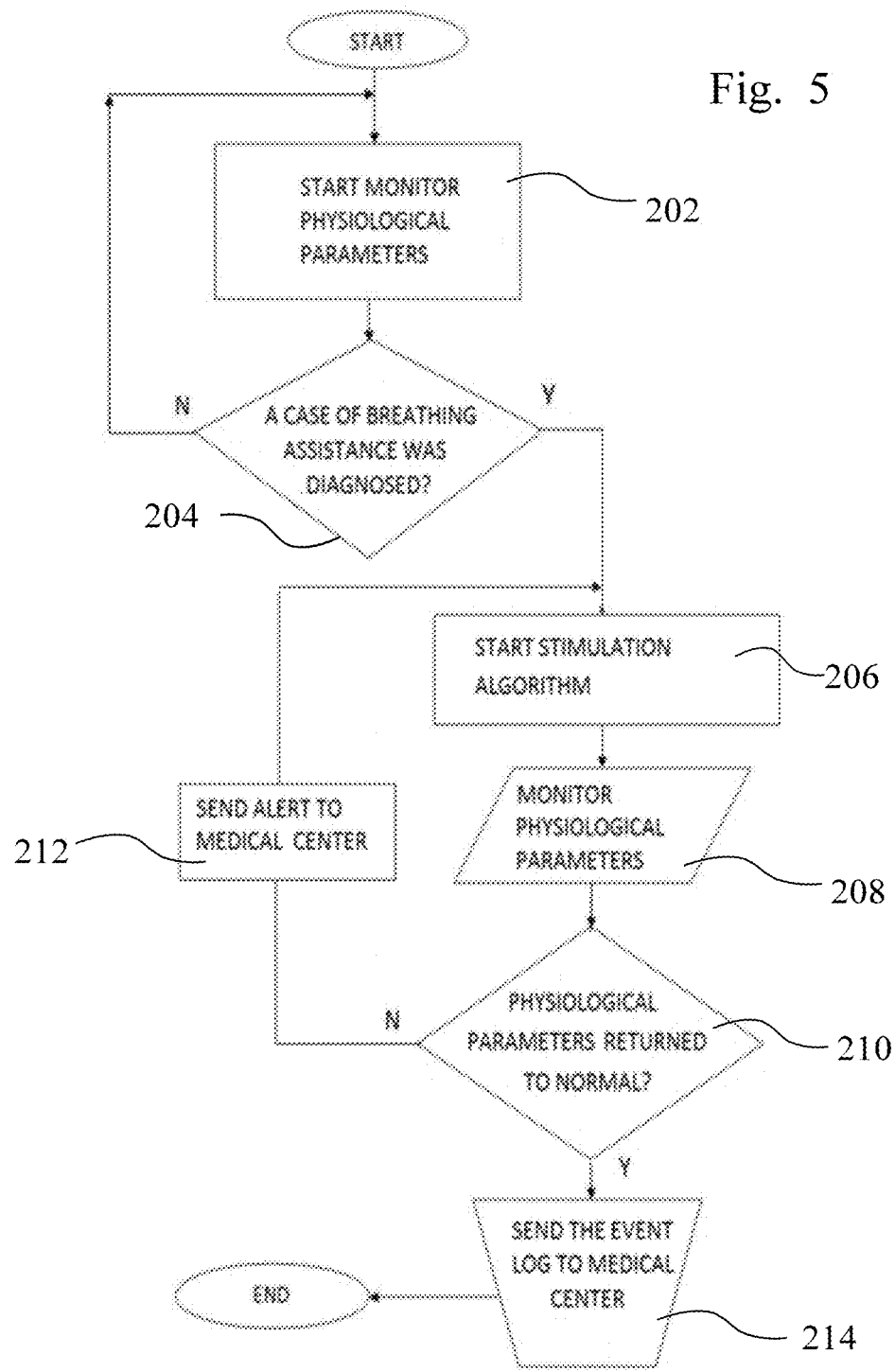
FIG. 5 is a flowchart of the second embodiment of the invention, showing the steps of the method.
Figure 6A:
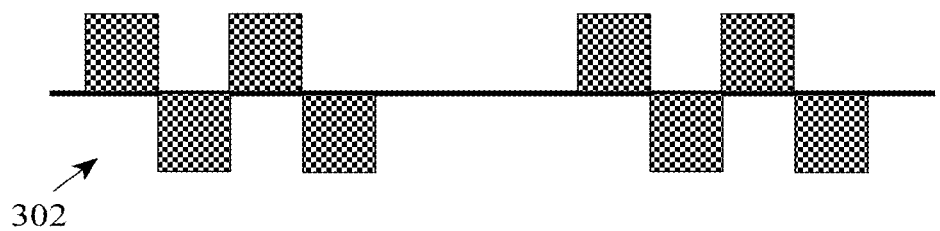
FIGS. 6A, 6B, 6C and 6D are diagrams of exemplary pulse trains such as the invention might employ.
Figure 6B:
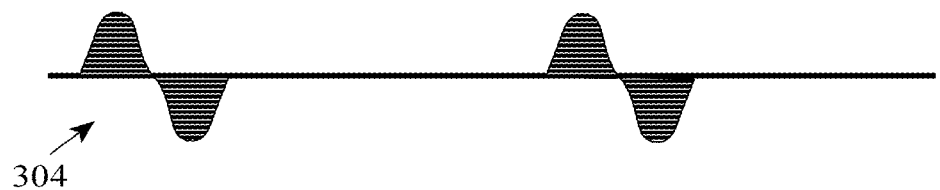
Figure 6C:
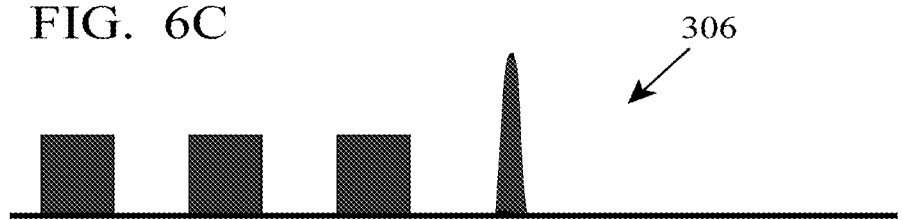
Figure 6D:
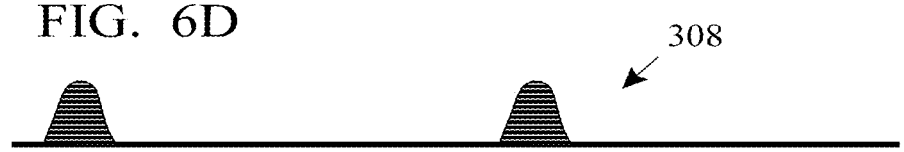

FIG. 5 is a flowchart of the second embodiment of the invention, showing the steps of the method.

The sleep apnea, snoring, emergency situations and breath assistance device of the invention will start of by monitoring physiological parameters such as blood pressure, blood oxygen level, heart rate and the like, shown at step 202. This may be done advantageously by means of a wrist unit, finger unit, a wearable fashionable fitness monitor or item of jewelry or sticker, or by a sensor on the torso under a garment, or a combination sensor/electrode on the torso, and so on.

If the sleep apnea, snoring, emergency situations and breath assistance device detects during monitoring that breathing assistance is required (step 204) then it may begin assistance at step 206, sending the pulse trains discussed elsewhere to some or all of the muscles implicated, as discussed above. Notice that the present invention muscle groups stimulated should not be confused either with the muscles of the throat or tongue (which are the area of the apnea occurrence) nor the diaphragm muscle, the usual muscle used in breathing.

Monitoring of the assisted breathing, 208, may continue for a prolonged period of time, waiting for the monitoring to show that the breathing returns to normal, which if it occurs is step 210. However, after a time-out period of some minutes has passed, if breathing has NOT returned to normal, than an alert to a medical center is made, step 212. Assuming that breathing does return to normal, the device nonetheless sends an event log entry to a medical center (step 214) for easy access by medical professionals.

Importantly the device may have an algorithm which analyzes the monitored data, and examines the stimulation history, and based upon the algorithm, then actually optimizes the parameters of the stimulation, thus providing a unique and optimized stimulation from moment to moment or from breath to breath.

Figure 11:
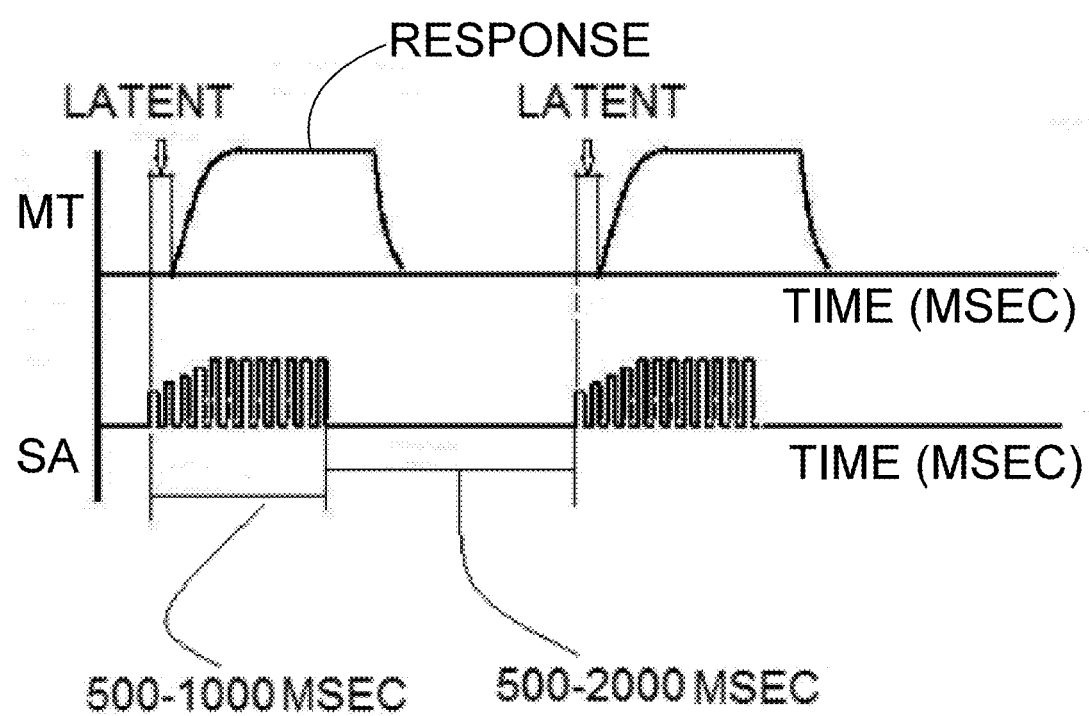
FIG. 11 is a pulse train sequence applied to the chest and/or abdominal muscles to induce either a stimulated breath or an assisted breath.

FIG. 11 is a view of a typical, exemplary, pulse pattern. The upper graph is muscle response "MR" while the lower graph is the stimulation pulses applied "SA". It may be seen that both horizontal axes are time in milliseconds. An increasing amplitude of pulses are provided by the electrodes transdermally to the person using the device. A latency period occurs as the stimulations of the muscles do not cause an immediate contraction of the muscle. The muscle then responds, making the "shark fin" shape on the top graphs, with an increased level of response triggered for a period of time.

Figure 12:
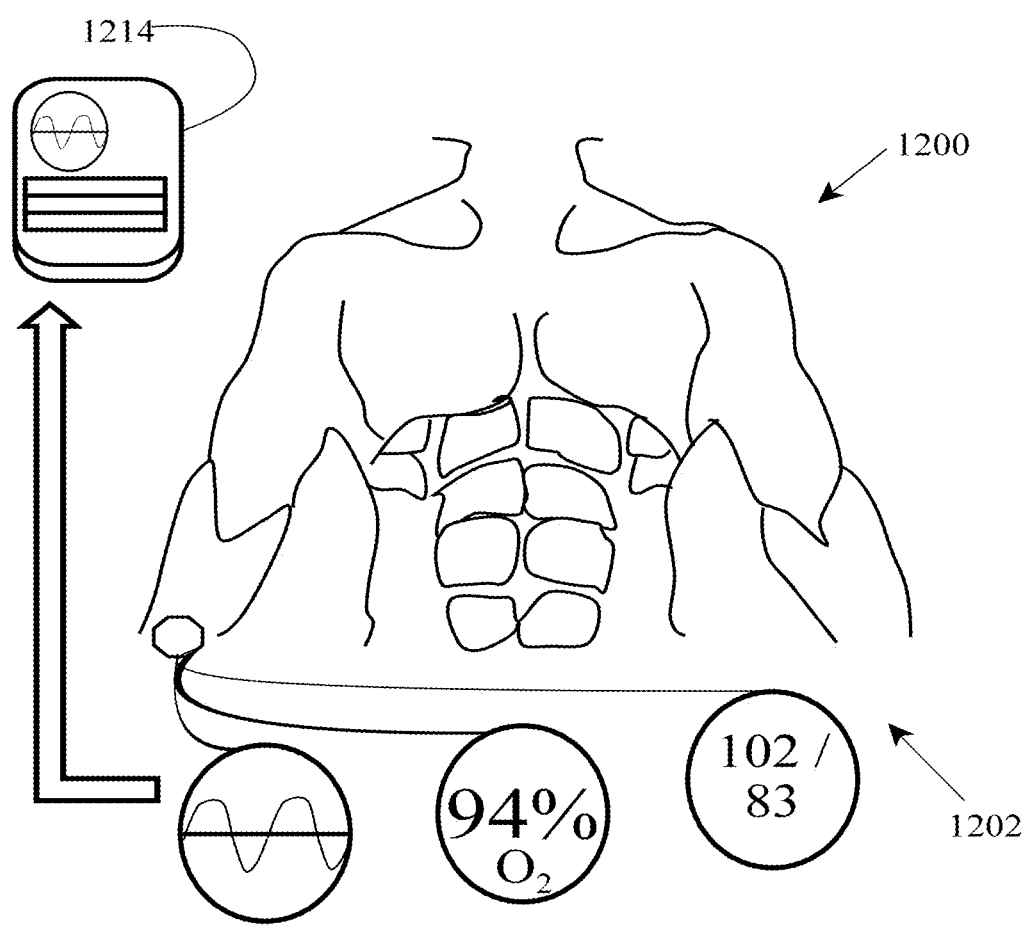
FIG. 12 is a block diagram showing three potential physiological parameters which might be monitored: blood pressure, heart rate (heart beat), and blood oxygen level.

FIG. 12 is a block diagram showing a person with a wrist monitor only, which wrist monitor may be monitoring, for example, heart rate, oxygen levels, or blood pressure. The selected parameter, in this case a heart rate, is sent to the control module (in this case the user's mobile device such as a tablet or telephone) and the control module may then carry out various operations: display to the user, saving of an event log entry, alerts to the medical center or even alerts to the person, or even, in some embodiments, control of a vehicle.

This stimulation of course has the effect of increasing the chances that the person will breath, and if the person does breath, the muscle tension artificially built up in the abdominal muscles or chest muscles will add to the power of the breath. It is important to understand that a muscle which has had the stimulation applied and has tensed up is likely to demonstrate a stronger breath than a muscle which has not been treated.

Note that the "wrist" monitor may be a bracelet, ring, a sticker, or other type of wearable monitor unit.

FIGS. 6A, 6B, 6C and 6D are hypothetical diagrams of exemplary pulse trains such as the invention might employ: these pulse trains are examples of individual pulses and thus are not the presently preferred embodiment, instead, these are "building blocks", low level pulse trains which might be used to create a variety of pulses as discussed above. Exemplary pulse trains 302, 304, and 306 have slightly different wave forms, amplitudes and frequencies from one another. Form 302 is a basic sine wave shape, repeated a minimal number of times, while 304 is a square wave. Wave from 306 is a further build: this wave form has one-half of each wave generated, followed by a different type of wave. Wave form 308 is another which has obviously been rectified. Thus in sequence, 304 can be used to build 306, which itself is a small example step toward the true presently preferred embodiment shown in FIG. 11.

Returning to FIGS. 4, 5, 6, 7, 8, 9, 10, 11, etc, it will be understood that this is susceptible to changes from the present parameters. In addition to preset parameters, the timing and types and amounts of stimulation may be changed by a heuristic (learning) control module or by external wireless controls, for example, by a preferred terminal used by a medical professional at a medical facility accessing the data files of the invention, analyzing the data including both input and output (stimulation and tension) and then altering the parameters wirelessly. The user may never even be aware that they have, by remote wireless access and control, "been seen by the doctor", and that their treatment regime has been improved or altered. Thus there are three modes or more of control enabled by use of the control module linked to a mobile device: a first mode of control by means of manual control input to the mobile device, for example, when a person is being seen or for a long-term person who supervises some aspects of their own care, secondly an adaptive heuristic control by an artificial intelligence module loaded in the mobile device, in which the AI monitors and alters the parameters of the care given automatically and without human interference, and third, remote control from a remote location via communication with the mobile device, as discussed earlier, in which a medical professional might "call" or "text" (or more likely access by data network such as 4G), to control the mobile device and thus the control module. In the presently preferred embodiment, it is anticipated that combinations of these three modes will be most useful, with an AI app in the mobile device, human controls for the person, and professional remote control all co-existing and being used routinely for the same person but on different schedules.

This may wireless access of data and control of parameters may occur at any time.

Figure 7:
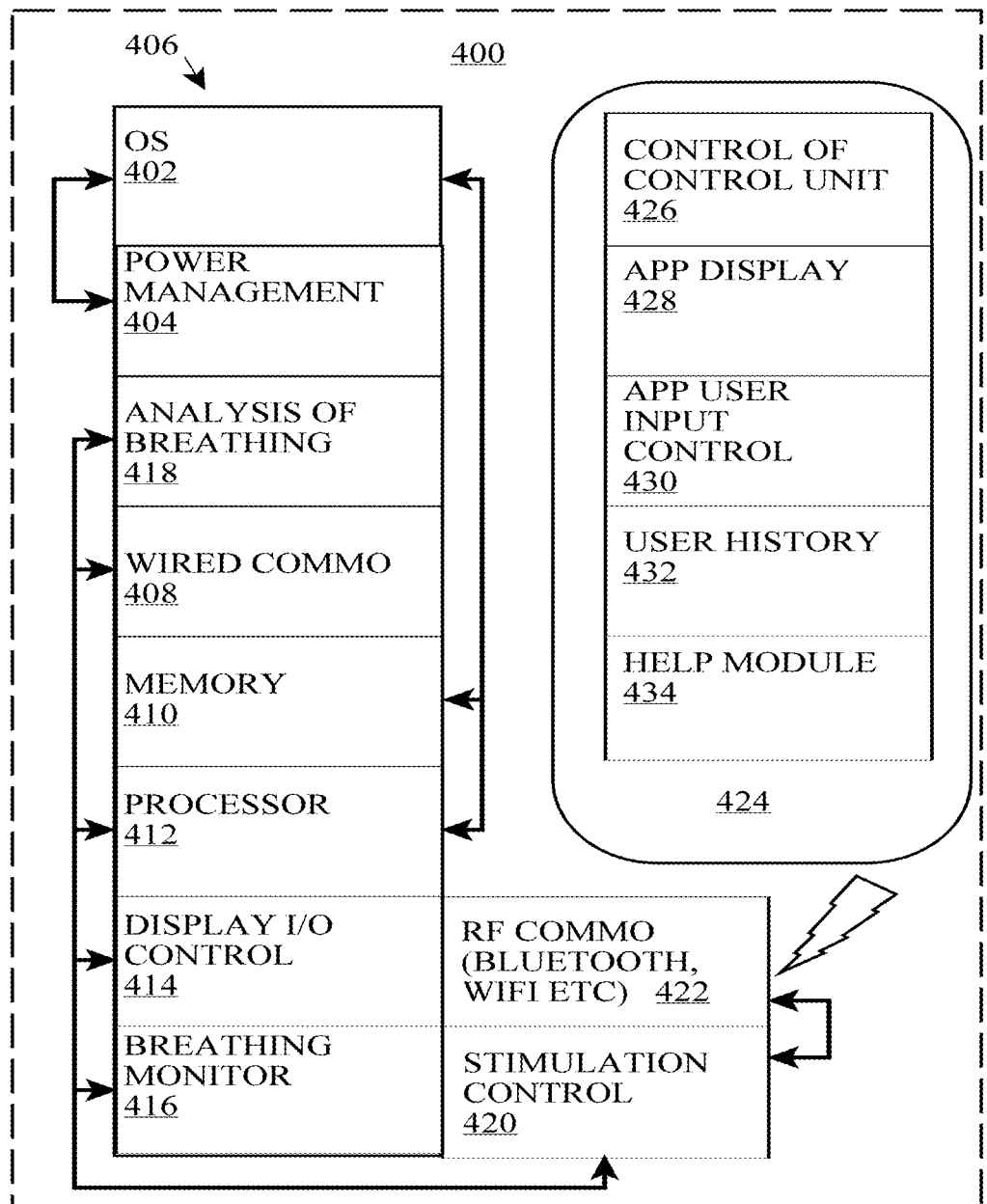
FIG. 7 is a block diagram of the modules of the invention in the control module and mobile device.

FIG. 7 is a block diagram of the modules of the invention in the control module and mobile device. System 400 may have two physical modules: the control module 406 (FIG. 4 item 114) and the mobile device 424 (FIG. 4 item 118). The may communicate either by wired communication or by means of wireless communication.

The control module 406 will have a number of modules and functionalities, which may be entirely mechanical, or partially programming stored in memory 410 and process by CPU 412. Operating system 402 may handle housekeeping chores such as inter-programing communications, power management 404, wired communication 408, access and management of the memory 410, as well as optional display screen control 414.

It will be appreciated that one preferred embodiment of the control module 406 will have a display screen, possibly a touch screen, allowing easy use of the control module without awkward controls and without requiring the mandatory use of a mobile device 424 as part of the system. Another embodiment may be part of the wrist/finger sensor.

Breath monitor 416 will receive data from the sensor (see FIG. 4 item 120) and pass that information to analysis module 418, which may save it to memory 410 and/or send it via commo 422/408 to mobile device 424 to be saved there. If the analysis module 418 has determined that stimulation of muscles to promote a breath is called for by pre-stored parameters or heuristic (learned) parameters, then stimulation control module 420 is activated to send via wired commo 408 (if the electrodes are wired) or RF commo module 422 (if the electrodes are also wireless) a command for a selected type of stimulation.

In general the RF communication module 422 may be used to receive instructions from, and provide data to the mobile device 424. Mobile device 424 will have at the top level a control module 426 which is distinct (see FIG. 7, item 406 versus item 426) from the largely hardware based control module 406. The "control function" 426 of the mobile device is obviously used to control the (largely hardware) control module 406, for example in embodiments of the control module 406 having no screen, or when the control module 406 (which is likely to be connected by leads and electrodes to the person's body) is out of sight underneath clothing. Also, note that while the control module 114

(see FIG. 4) is depicted to be larger than the mobile device 118, it is most likely that the control module 114 will actually be much smaller than a mobile device, so as to make it easy and unobtrusive for the person to wear. The smaller control module 114/406 in turn makes the use of a mobile device 118/424 more desirable as it will be easier to control: smaller units have less space for soft buttons, hard buttons and so on.

App display module 428 simply provides the wearer or medical user with information while app user input control module 430 allows the user to actively enter control instructions into the control module 406 using the mobile device. User history module 432 may be useful in diagnostic or personal health scenarios, while help module 434 assists the user with control of the device, understanding of their medical situation and so on.

One possible embodiment of the invention is for the control module 406 to be an entirely electrical device with little or no programming (for example, no CPU, no memory, and all other functions based on hardware, with the various analysis and control modules such as 418, 416, and 420 moved to the mobile device 424. Mobile device 424 in turn may be the person's own cellular telephone, with an app encompassing all of the electronic programming functions of the invention. In this embodiment, the hardware only control module 114/406 may still be sufficient to operate the system for breath assistance for an extended period of time with nothing but electrical circuits for supervision by the unit.

FIG. 8 is a simple data structure as might be used by the sleep apnea, snoring, emergency situations and breath assistance device to assist therapeutic activities, to test the device or to optimize usage of the device for a given person or condition. Event 500 might be a single instantiation of a data structure which has a new instance created and added to a database at each event 500. The trigger for the creation of the event entry 500 might be a physiological event such as a breath, a period of occluded breathing, a certain time of day, and so on and so forth. Time & Date field 502 might further include indicia of the duration of the event, autonomic breath monitored data 504 might provide the data collected by the sensor (see 120 on FIG. 4). Pulse train stimulation applied type 506, applied duration 508, frequency 510, and amplitude 512 are all typical information which might be stored to describe a single application of the electrodes to the muscles. Assisted breath monitored data 514 may provide the same sensor data as field 504, but for the time period of an assisted breath, as a measurement against baseline of how effective any particular stimulation had been.

Figure 9:
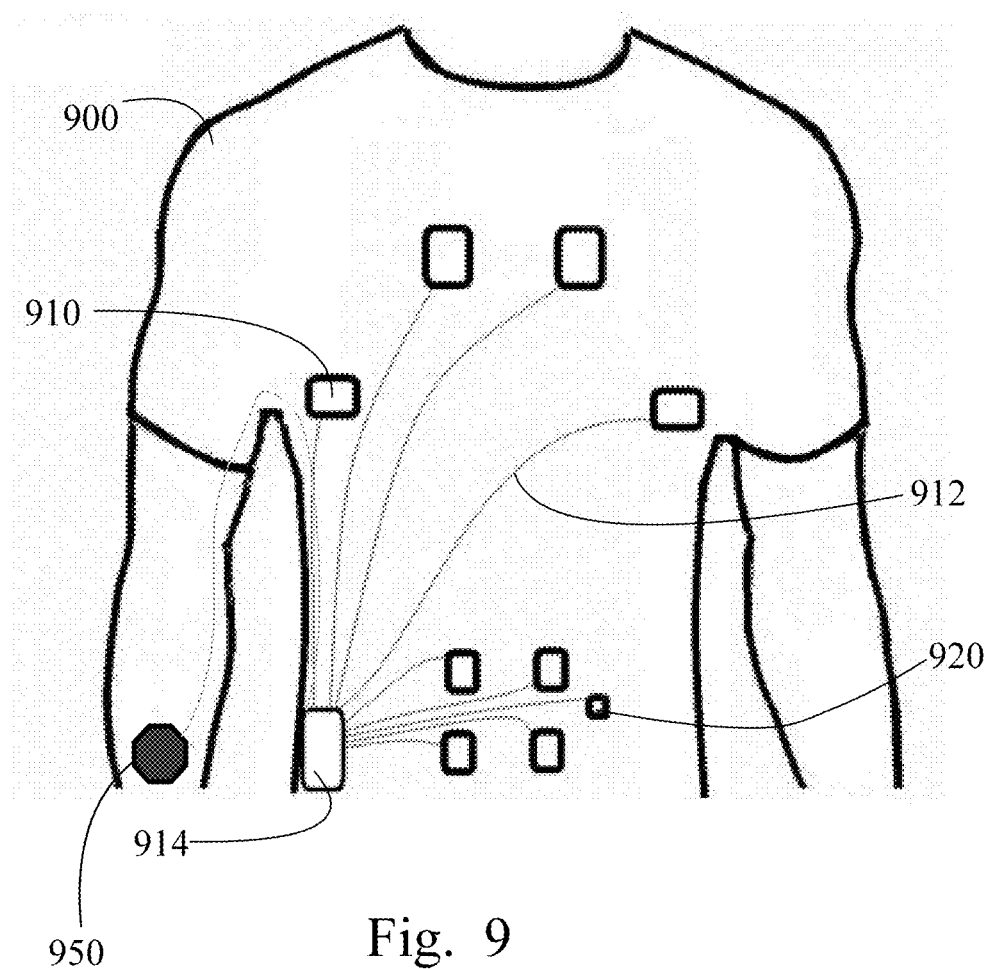

FIG. 9 is a transparent frontal view of a person wearing the present invention device, showing the sleep apnea, snoring, emergency situations and breath assistance device worn inside of an ordinary garment 900, which may be a t-shirt, shirt, wrap, blouse, sweater, harness or the like. Garment 900 is chosen for the figure because it can be seen to be a very thin, small type, such as a child might wear while sleeping.

Despite the small size of the garment 900, dermal electrode pads 910, leads 912, monitor 920 and even control module 914 can all fit inside of the garment, against the wearer's body. Note that in the case of monitors 920 and 950 and electrodes 910, this may be a requirement for operation of the devices (the garment might be an insulator or impedance). Monitor 920 may be optional, monitor 950 may be a pulse oximeter, or other type of direct breathing monitor or monitor of other parameters which indirectly depend upon breathing.

Figure 10:
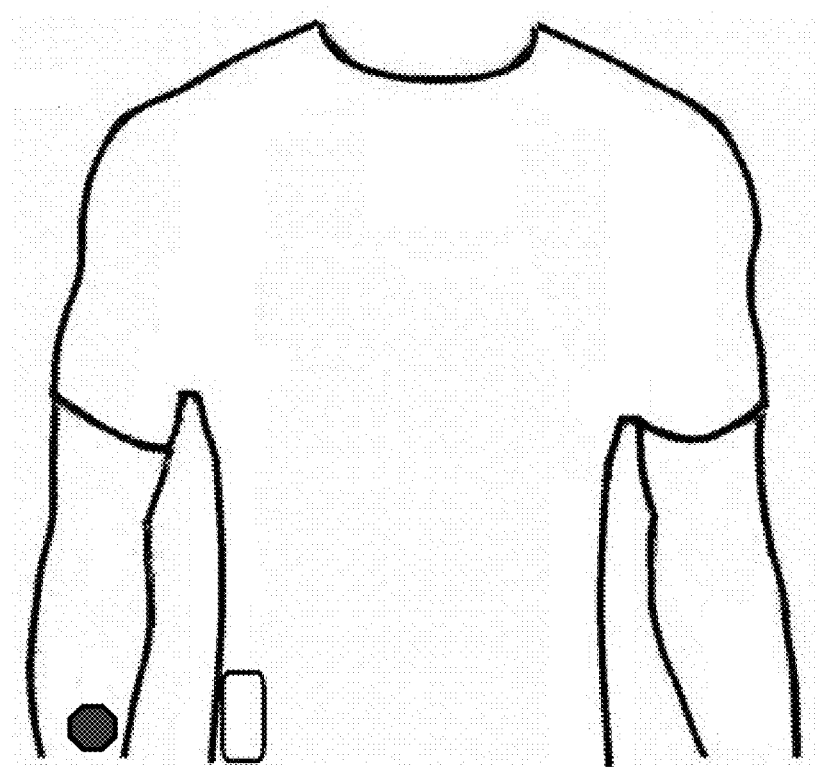
FIG. 10 is a non-transparent frontal view of a person wearing the present invention, showing the actual front view (outside view) of the person wearing a garment, if they wear the control module visibly, and if they are wearing a wrist-style breathing monitor.

This aspect of the sleep apnea, snoring, emergency situations and breath assistance device has enormous benefits. The small size of the device means that the device can be easily and inconspicuously worn while sleeping. FIG. 10 is a non-transparent frontal view of a person wearing the present invention, showing the actual front view (outside view) of the person wearing a garment, if they wear the control module visibly. In this case, it may be seen that there is nothing but the small control module and the small pulse oximeter visible. A person wearing the device may easily have a comfortable night sleep, especially compared to the device of PRIOR ART FIG. 1.

In embodiments, even the control module may be located inside of the garment, or inside of a special garment, on the wrist/finger monitor, etc.

FIG. 9 and FIG. 10 also show a wrist mounted breathing sensor. The breathing sensor may be attached by means of wires, (FIG. 9) or may be wirelessly connected (FIG. 10), or connected by means of a wifi network, to the control module 914 to provide information. Note that in this embodiment, the monitor 920 may be optional, with it's functions taken over by the wrist sensor. The wrist sensor might be tracking breathing or oxygen levels and passing this, on request, to the control module either directly by BlueTooth® or other short-range wireless, or indirectly by short range wireless to the user's telephone/tablet, which then passes the desired information to the control module.

Figure 21:
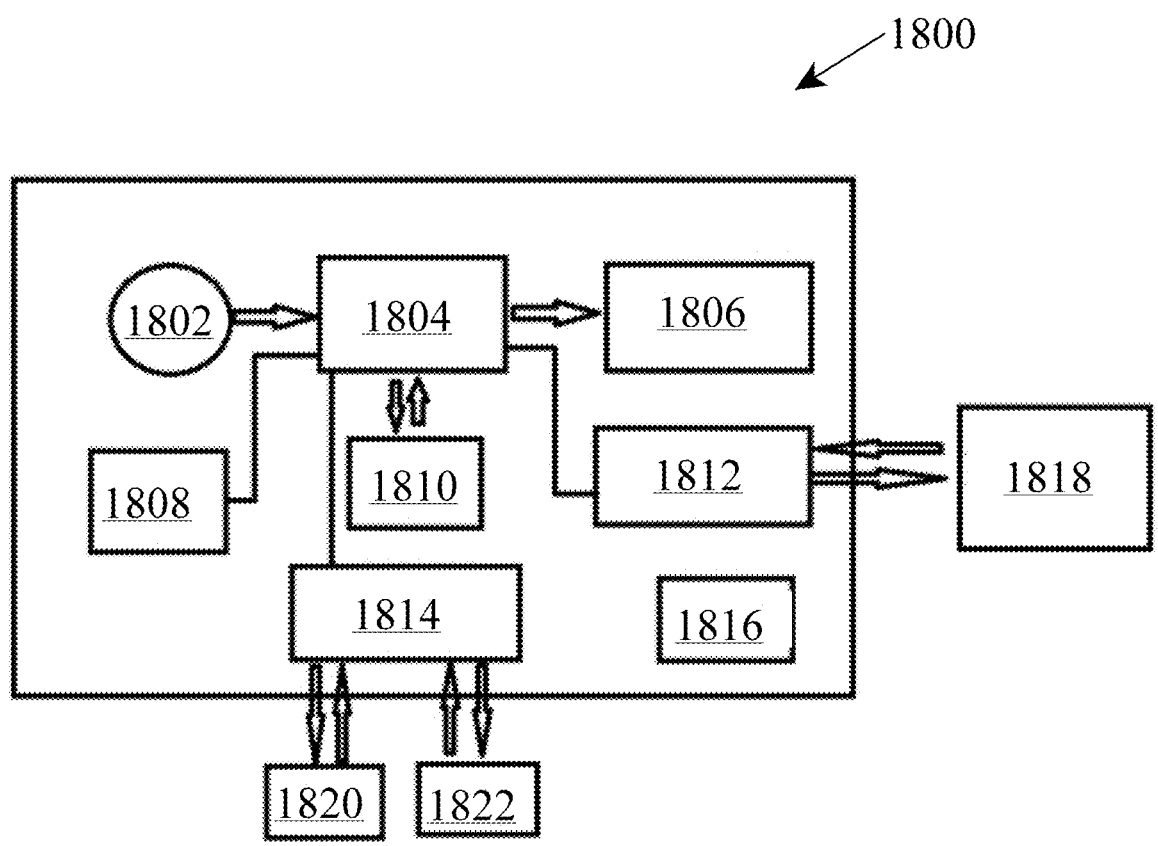
FIG. 21 is a block diagram of a unit which can communicate with vehicles easily.
Figure 22:
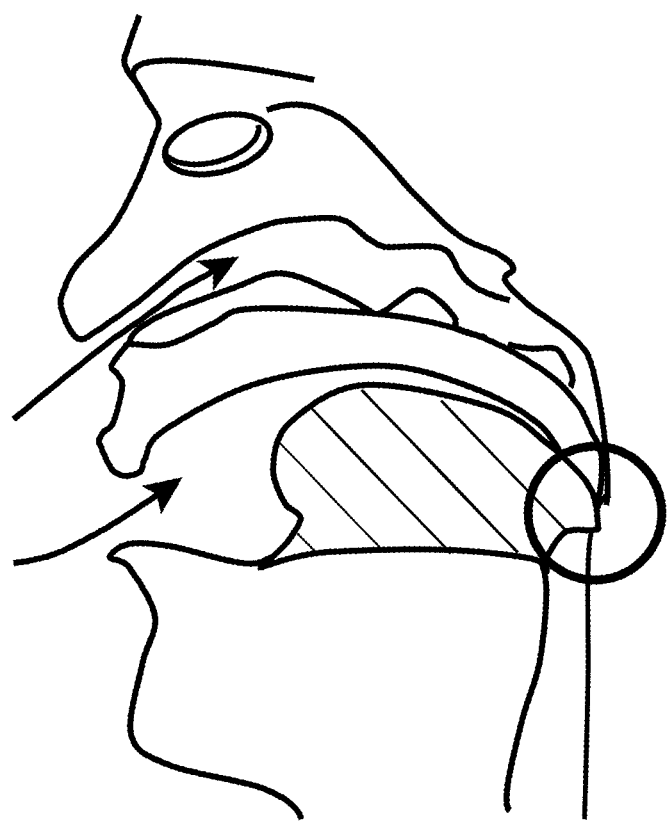
FIG. 22 shows the rear end of the tongue has relaxed backward into the throat, blocking it in typical sleep apnea, labeled PRIOR ART.

For this application, the word driver is defined to be "a person in a job requiring attention and focus", and in fact anyone in any job requiring attention and focus, such as pilots, truck drivers, bus drivers, but also including life guards, prison guards, medical professionals, air traffic controllers, and so on. FIG. 21 is a block diagram of a unit which can communicate with vehicles easily: safety device 1800. The safety device 1800 may be a standalone device, or it may communicate, for example by means of V2X protocol (see module 1812), or other wireless or wired protocols (1814), with an autonomous vehicle 1818. When the user is found by bio sensor 1802 to be sleeping or in a lower state of awareness (likely indicating that the user is asleep and having an apnea event) as determined by CPU 1804 using instructions from NV memory 1810, the user is stimulated via internal electrode 1808 with the pulse train, the device may communicate this to the vehicle 1818, and provide instructions to the vehicle 1818, for example, to apply the brakes, pull to the side of the road at a safe location for parking, apply the emergency/distress lights, or even simply assume control of driving the vehicle to a present location such as the user's home address, the medical center, a police station, or the like.

A display 1806 may provide information to the driver/essential personnel should they wake up, or for user programming, information, or for use by health professionals, a preferred terminal (such as a device support specialist's computer or a health professional's mobile device/computer, etc). This display 1806 will be most useful when the sleep apnea, snoring, emergency situations and breath assistance device is a standalone device with no other control units. In other embodiments, a mobile phone/mobile device 1822 however may be more suited for both output and input, if provided with a suitable app for this purpose. Optionally the sleep apnea, snoring, emergency situations and breath assistance device may communicate to a control module 1820 similar to the control module discussed previously, or may be a stand alone device.

It may be powered by battery 1816 or the like.

The unit may be mounted on other parts of the arm than the wrist: upper arm, lower arm, hand, finger, etc, in the form of jewelry (bracelet, ring, etc) or adhered to the skin (sticker, electrode, decal, body jewelry, etc).

Internal electrode 1808 may be mounted in the arm mounted module so this electrode is stimulating the user's arm, wrist, finger, hand, etc, and in this option the device may optionally not have any chest mounted or torso mounted electrodes.

Thus the sleep apnea, snoring, emergency situations and breath assistance device may be configured to work by itself, with no garment or torso mounted electrodes, or it may work with a vehicle, or with a mobile device, or with a control unit/garment, or with all of these or a combination thereof.

Figure 13:
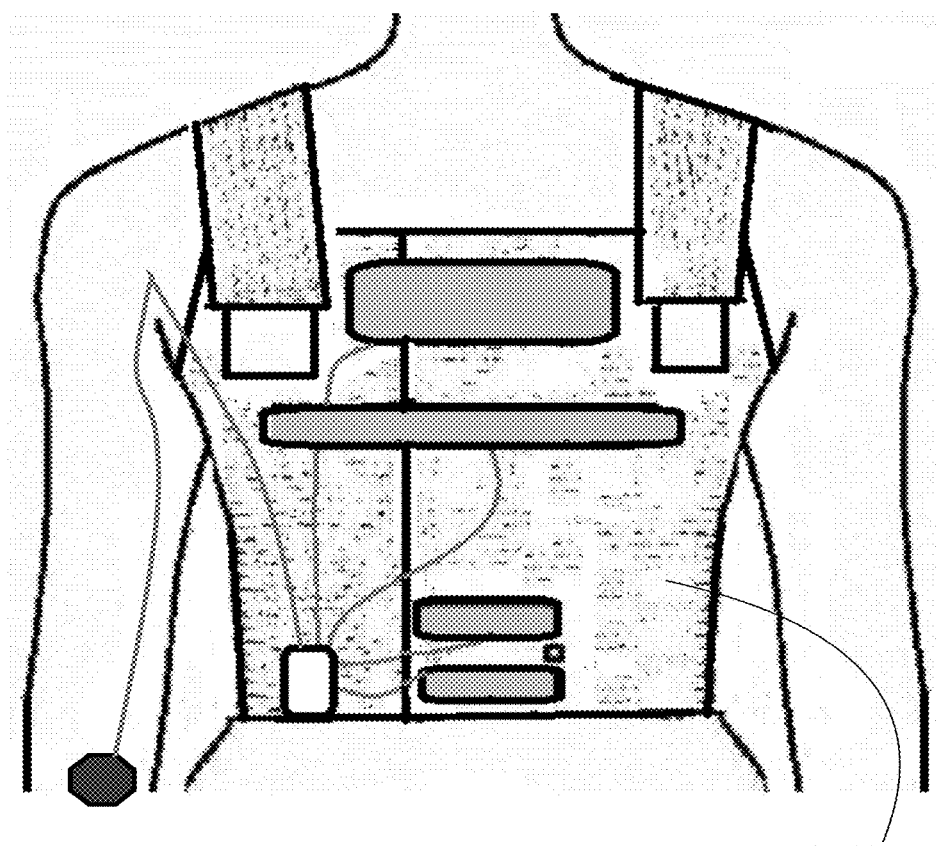
FIG. 13 is a view of a garment for wearing the invention in a snug and inconspicuous manner.

FIG. 13 is a view of a garment for wearing the invention in a snug and inconspicuous manner. Garment 1360 may be a simple band worn about the torso, such as seen in parts of this figure, or may be a more complete garment which covers most of the torso, much like a shirt, corset, tank top, or the like. In either case, the garment will hold snugly at least one electrode, rendering the electrode both secure and also less easy to see. This is another aspect of the invention which will be especially beneficial to youth, who may wish to avoid standing out amongst their peers.

Notice that the user is again employing a wrist sensor.

In one important aspect, the garment may be used to hold one or more zone stimulators.

Figure 14:
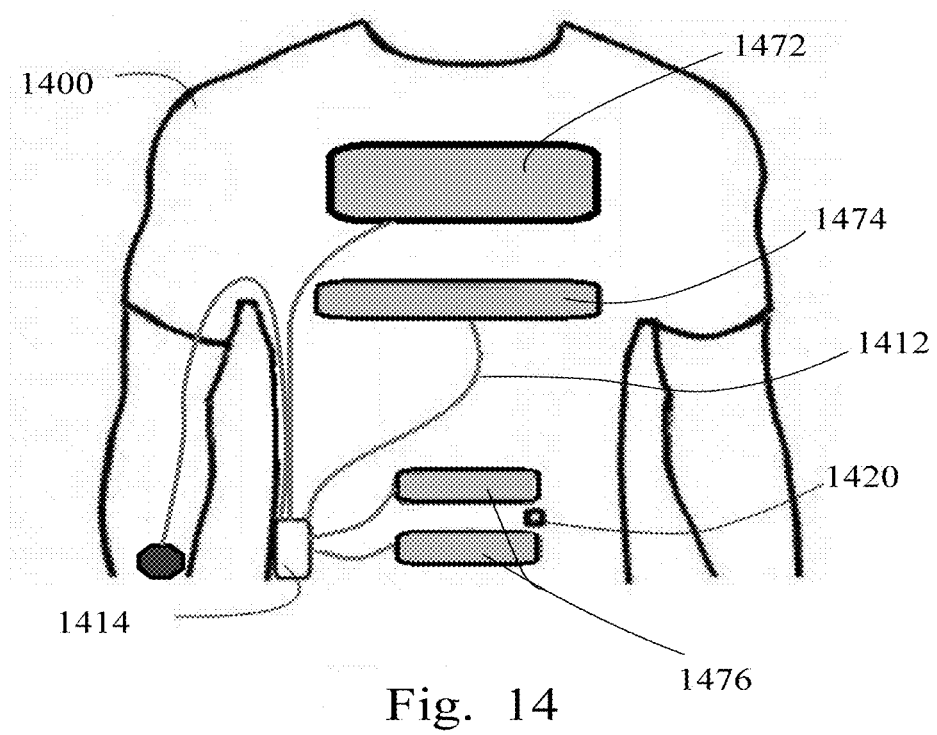
FIG. 14 is a transparent frontal view of a person wearing a second embodiment of the present invention device, showing the device worn inside of an ordinary garment such as a t-shirt, wrap or the like, and with larger zone stimulators. In this embodiment the wearer is using a smaller and more stylish "fitness monitor" type wrist monitor.

FIG. 14 is a transparent frontal view of a person wearing a second embodiment of the present invention sleep apnea, snoring, emergency situations and breath assistance device, showing the device worn inside of an ordinary garment, and with larger zone stimulators or zone electrodes instead of normal electrode pads. In the case of a long sleeved shirt, sweater, blouse, wrap or the like, even the wrist mounted monitor (or an arm mounted sensor) would not be visible.

Figure 15:
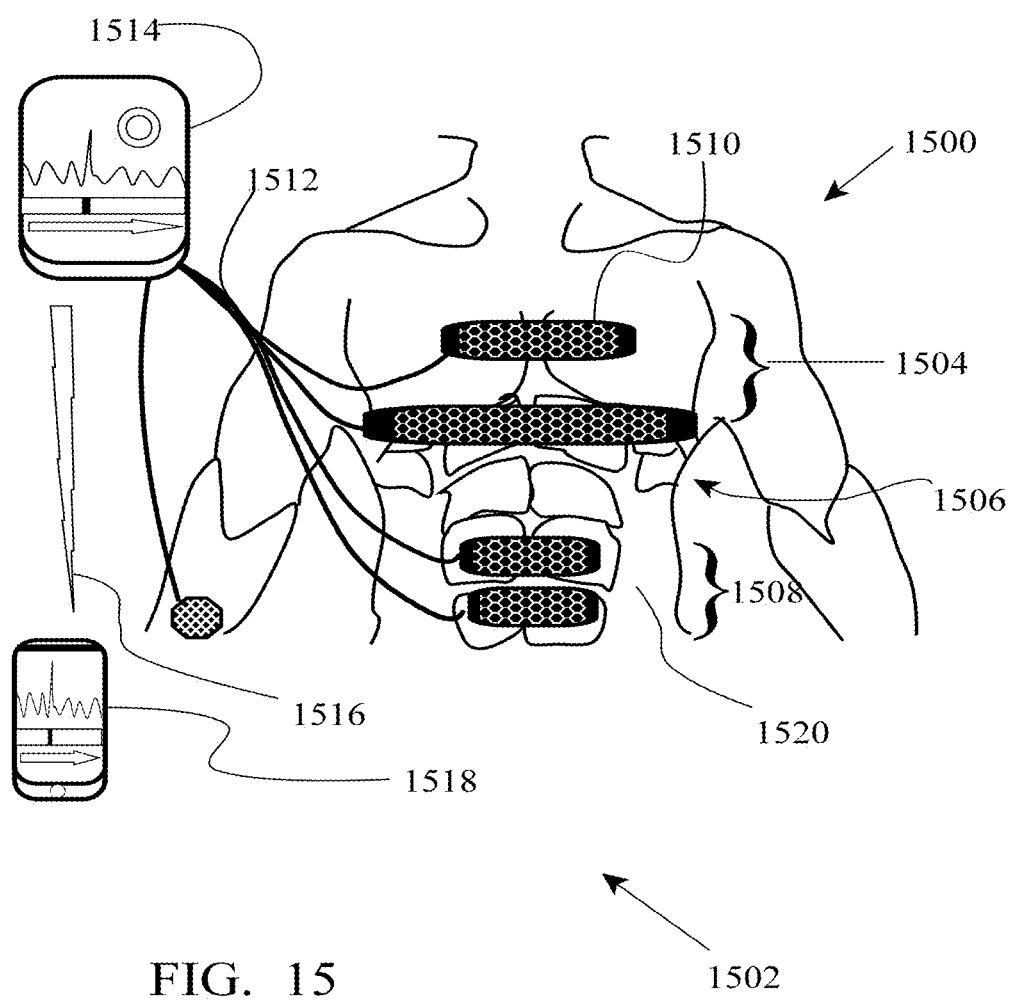
FIG. 15 is a front view of the second embodiment of the invention showing more detail of the muscle groups and the zone stimulators of the invention.

FIG. 15 is a front view of the second embodiment of the invention showing more detail of the muscle groups and the zone stimulators/large enough stimulators of the invention. FIG. 14 includes a garment, whereas FIG. 15 includes more components and shows the muscle groups as well.

Testing of the invention has revealed that normally size electrodes (which tend to be perhaps one centimeter across in the center and only a few centimeters across total) may not be as effective at causing muscle response as much larger stimulators. Thus the term "large enough" electrodes is used herein to denote electrodes which are large enough to cause muscle response. The larger/large enough electrodes of the invention may be as much as several centimeters or several inches across, and may be used in multiples (for example 2 large electrodes in a single fabric enclosure) so as to function as even larger electrodes.

The present invention also teaches a ZONAL stimulator pad which covers a substantial part of a muscle group, as shown in FIG. 14. Person 1400/1500 has a control module 1414/1514 and a sensor/monitor 1420/1520 as previously described, as well as an RF (1516) control device 1518—but the stimulators are much different than the previous embodiment.

Each zone electrode may have one, or preferably more than one electrode(s) (electrodes large enough to efficiently stimulate a large muscle) within it as an inner layer. The large electrodes within the zone electrode may be in contact with the skin directly, while the zone electrode has a large fabric enclosure as a second layer on the outside of the electrodes, insulating the electrodes (the fabric has insulating properties) from contact with garments, other body parts, etc.

Zone "A" (pectoralis) stimulator pad 1472/1510 may be seen to be large enough to cover substantial parts of the pectoralis muscles 1504. Testing has shown that larger areas of stimulation provide better muscle response to the stimulation, and so the stimulator pad 1472 is sized to be as much as one quarter or one half or more of the area of the muscle group. In this case, one pad spans both pectoralis muscles.

Zone "B" (serratus) stimulator pad 1474 may be seen to span a much larger area than two small electrodes could, or even more than a whole group of normal sized electrodes could possibly cover. The zone stimulators of the invention stimulate larger areas of the muscles 1506, resulting in much larger stimulations of the various reflexes such as the contraction in the muscles 1506/1504.

Zones "C" and "D" (abdominal) stimulators 1476 stimulate the abdominal muscles 1508. These dermal zone stimulation pads (1510, etc) provide much better breath responses as well: the muscle is stimulated much more strongly than it would be with ordinary electrodes.

Leads 1512 connect the zonal stimulators/zone electrodes to their control devices.

Figure 16:
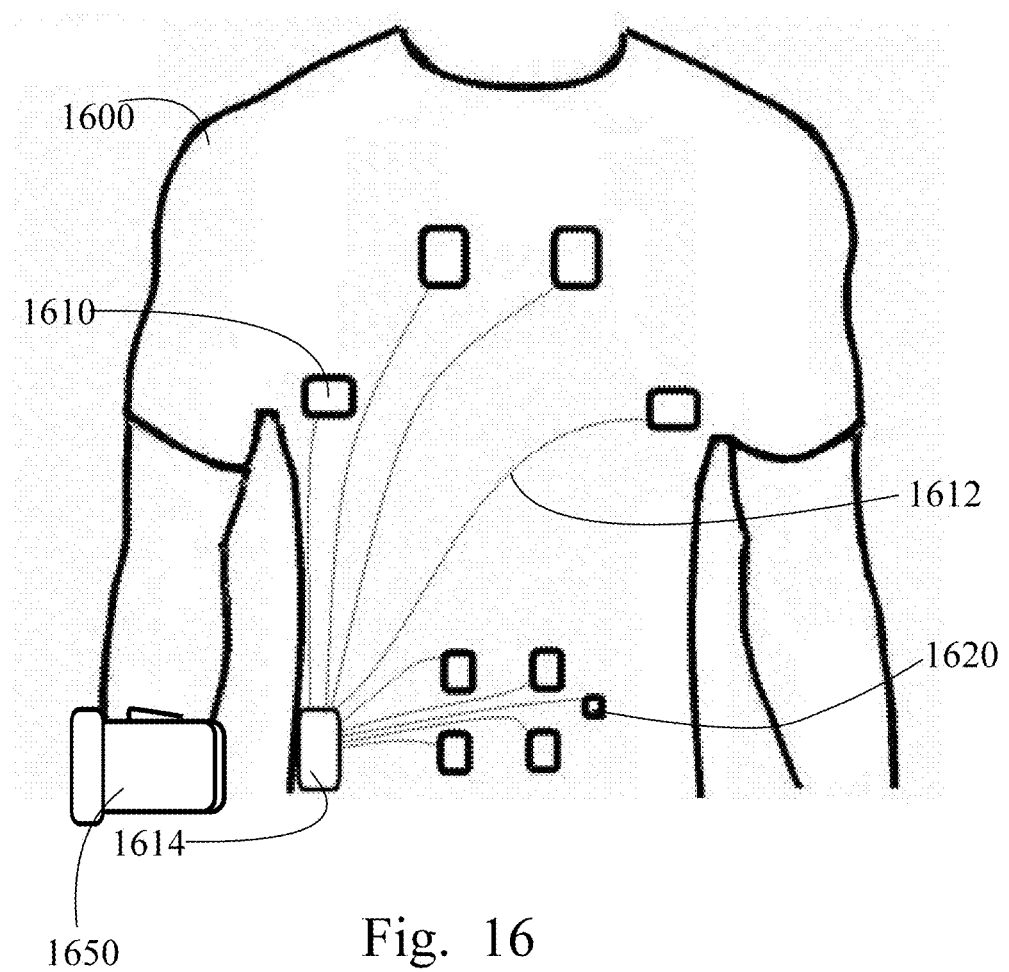

FIG. 16 is a transparent frontal view of a person wearing an embodiment of the present invention device, showing the device worn inside of an ordinary garment, and with a wrist monitor of a larger type able to accurately measure blood pressure as well as breathing, pulse, oxygen levels and the like. Wrist mounted measuring devices are known which can actually track additional information such as blood pressure, the same holds for finger mounted devices. While such measurements are believed to be unnecessary to the preferred embodiment of the invention (the preferred embodiment is a wrist/finger/arm oximeter), these embodiments are more useful for gathering additional medical data, for example, for monitoring a patient who has additional health concerns (for example low blood pressure), or for gathering scientific data and so on.

Figure 17:
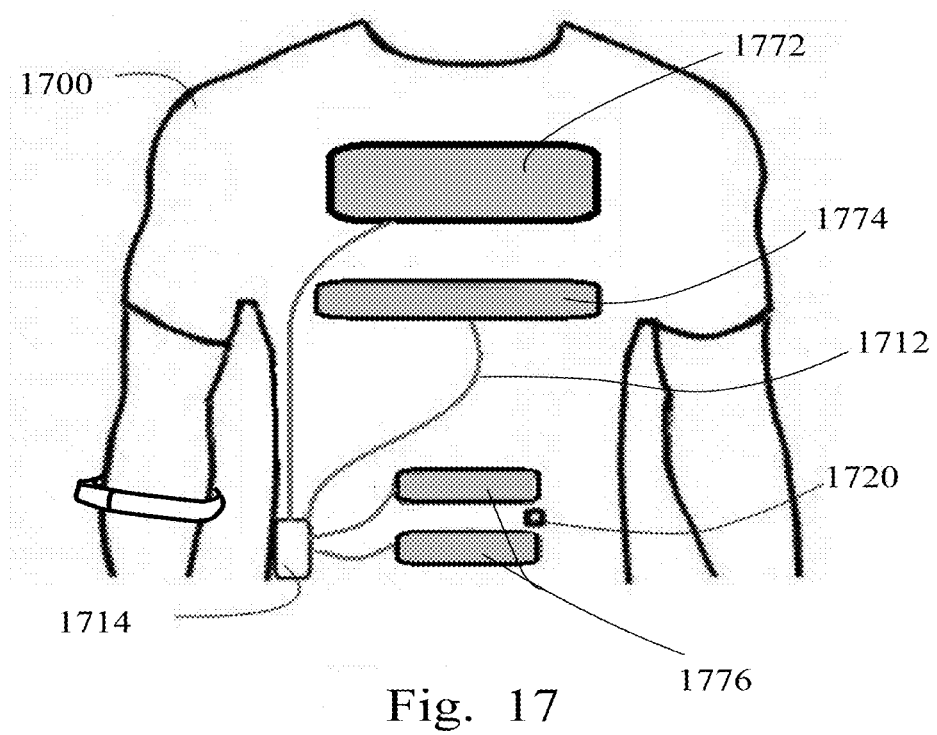
FIG. 17 is a transparent frontal view of a person wearing another alternative embodiment of the present invention device, showing the device worn inside of an ordinary garment with larger zone stimulators. In this embodiment the wearer is using a smaller and more stylish "fitness monitor" type wrist monitor.

FIG. 17 is a transparent frontal view of a person wearing another alternative embodiment of the present invention device, showing the sleep apnea, snoring, emergency situations and breath assistance device worn inside of an ordinary garment with larger zone stimulators. In this embodiment the wearer is using a smaller and more stylish "fitness monitor" type wrist monitor designed to be sleek and fashionable, resembling a fitness tracking device such as a FitBit® or the like. The sensor may even be a fitness tracking device of standard type, which is queried by the control module for the desired information. For example, the fitness tracker might be tracking breathing or oxygen levels and passing this, on request, to the control module either directly by BlueTooth® or other short-range wireless, or indirectly by short range wireless to the user's telephone/tablet, which then passes the desired information to the control module.

Figure 18:
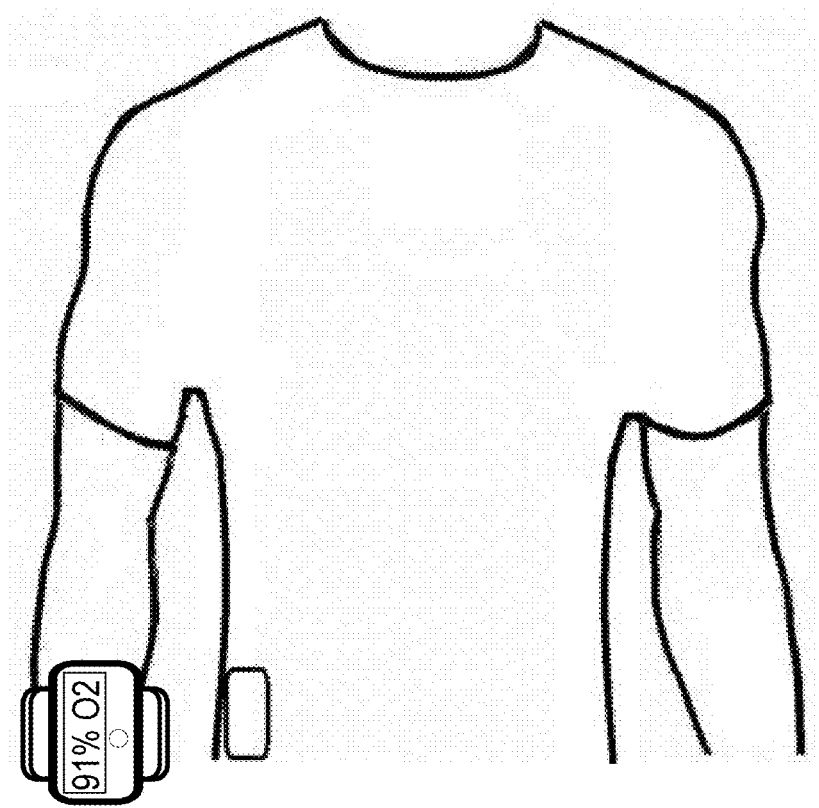
FIG. 18 is a frontal view of a person wearing yet another embodiment of the invention with a large enhanced visibility oxygen level monitor.

FIG. 18 is a frontal view of a person wearing yet another embodiment of the invention with a large enhanced visibility oxygen level monitor. Such an alternative embodiment might be useful for human monitoring, for example, for a parent to monitor a child, or a caregiver to monitor an elderly person, or even for an elderly person, who might have difficulty using a cell phone (or even difficulty reading small letters).

The disclosure is provided to render practicable the invention by those skilled in the art without undue experimentation, including the best mode presently contemplated and the presently preferred embodiment. Nothing in this disclosure is to be taken to limit the scope of the invention, which is susceptible to numerous alterations, equivalents and substitutions without departing from the scope and spirit of the invention. The scope of the invention is to be understood from the appended claims.

Methods and components are described herein. However, methods and components similar or equivalent to those described herein can be also used to obtain variations of the present invention. The materials, articles, components, methods, and examples are illustrative only and not intended to be limiting.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art.

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples. It is intended that the specification and examples be considered as exemplary only, with a true scope and spirit of the invention being indicated by the following claims.

What is claimed is:

1. A sleep apnea, snoring, emergency situations and breath assistance device configured for use by a person having a body, skin, a mouth, airways, first, second, third, and fourth pairs of abdominal muscles, and four chest muscles including first and second pectoral muscles and first and second serratus anterior muscles, the sleep apnea, snoring, emergency situations and breath assistance device comprising:
   a control module having operative electrical connections to a plurality of dermal electrodes configured to be attached to such skin of such person, whereby the control module is in communication with the dermal electrodes, the control module configured so as to be worn on such person's body;
   a first one of the plurality of dermal electrodes configured to be disposed on such skin of such person at one such chest muscle;
   a second one of the plurality of dermal electrodes configured to be disposed on such skin of such person at one such abdominal muscle;
   each of the dermal electrodes configured to deliver a plurality of pulse trains to one such respective muscle;
   the control module having a stimulation module operative to send a first pulse train to such chest muscle and a second pulse train to such abdominal muscle;
   the first pulse train operative to stimulate such chest muscle so as to cause a first contraction of such chest muscle;
   the second pulse train operative to stimulate such abdominal muscle so as to cause a second contraction of such abdominal muscle;
   whereby at least one breath is stimulated.

2. The sleep apnea, snoring, emergency situations and breath assistance device of claim 1, configured for use with a garment worn on such body by such person, wherein: the control module, the dermal electrodes and the operative electrical connections are configured so as to be worn on such body concealed within such garment.

3. The sleep apnea, snoring, emergency situations and breath assistance device of claim 2, further comprising:
   a third one of the plurality of dermal electrodes configured to be disposed on such skin of such person at a second such abdominal muscle;
   a fourth one of the plurality of dermal electrodes configured to be disposed on such skin of such person at a third such abdominal muscle;
   a fifth one of the plurality of dermal electrodes configured to be disposed on such skin of such person at a fourth such abdominal muscle;
   the control module further operative to send the second pulse train to such second, third and fourth abdominal muscles.

4. The sleep apnea, snoring, emergency situations and breath assistance device of claim 3, further comprising:
   a sixth one of the plurality of dermal electrodes configured to be disposed on such skin of such person at a second such chest muscle;
   a seventh one of the plurality of dermal electrodes configured to be disposed on such skin of such person at a third such chest muscle;
   an eighth one of the plurality of dermal electrodes configured to be disposed on such skin of such person at a fourth such chest muscle;
   the control module further operative to send the first pulse train to such second, third and fourth chest muscles.

5. The sleep apnea, snoring, emergency situations and breath assistance device of claim 4, the pulse train further comprising:
   a group of pulses consisting of a plurality of individual pulses increasing in amplitude with time, the group of pulses having a duration of 500 ms to 900 ms;
   a second time out period of 2 to 3 seconds during which no pulses are sent;
   repetitions of the group of pulses and the second time out period for a breath assist time period defined to last either until an autonomic breath occurs or for a period of time of no more than 3 seconds.

6. The sleep apnea, snoring, emergency situations and breath assistance device of claim 5, further comprising:
   at least one pulse oximeter configured to be attached to such user;
   the pulse oximeter sensor in operative communication with the control module;
   the control module further comprising an analysis module operative to receive a data from the pulse oximeter sensor and analyze the data to determine if such person is exhibiting an autonomic breath and if such person is not exhibiting an autonomic breath for a period of 3 seconds, the control module further operative to send the pulse trains.

7. The sleep apnea, snoring, emergency situations and breath assistance device of claim 6, wherein the pulse oximeter sensor is further operative to alert such person by means of a signal when it sends such pulse trains.

8. The sleep apnea, snoring, emergency situations and breath assistance device of claim 5, further comprising:
   at least one breath sensor in operative communication with the control module, the breath sensor configured to be disposed on such skin of such person;
   the control module further comprising an analysis module operative to receive a data from the breath sensor and analyze the data to determine if such person is exhibiting an autonomic breath and if such person is not exhibiting an autonomic breath, the control module further operative to send the pulse trains.

9. The sleep apnea, snoring, emergency situations and breath assistance device of claim 5, further comprising:
at least one blood oxygen level sensor, the blood oxygen level sensor in operative communication with the control module, the blood oxygen level sensor configured to be disposed on such skin of such person;
the control module further comprising an analysis module operative to receive a data from the blood oxygen level sensor and analyze the data to determine if such person is exhibiting an oxygen level indicative of a normal breathing pattern and if such person is not, the control module further operative to send the pulse trains.

10. The sleep apnea, snoring, emergency situations and breath assistance device of claim 9, further comprising:
an RF communication module;
the control module having a non-volatile memory and a central processor unit, the analysis module stored in the non-volatile memory, the control module having a start button operative to activate the sleep apnea, snoring, emergency situations and breath assistance device to begin an operating cycle, using a first set of preset operating parameters also stored in the non-volatile memory;
a mobile device having an operative RF connection to the RF communication module of the control module and further having a touch screen operative to display a set of data collected by the device and enable control of the secretion clearance and cough assistance device;
the start button further operative to establish the operative RF connection to the mobile device;
the mobile device having a module operative to provide wireless control of the operation of the control module;
the mobile device operative to collect data, provide for wireless setup and wireless maintenance of the breath assistance device.

11. The sleep apnea, snoring, emergency situations and breath assistance device of claim 10, wherein the mobile device is operative to provide control of the control module by one mode selected from the group consisting of: manual control input to the mobile device and the control module, manual control input to the mobile device and from the mobile device to the control module, adaptive heuristic control by an artificial intelligence module loaded in the mobile device and the control module, adaptive heuristic control by an artificial intelligence module loaded in the mobile device and from the mobile device to the control module, remote control from a remote location via communication with the mobile device and from the mobile device to the control module, and combinations thereof.

12. The sleep apnea, snoring, emergency situations and breath assistance device of claim 10, wherein the control module is further operative to alert such person by means of a signal from such mobile device when it sends such pulse trains.

13. The sleep apnea, snoring, emergency situations and breath assistance device of claim 10, configured for use with a vehicle being driven by such person, such vehicle having autonomous driving capability, wherein the control module further comprises:
a communication protocol allowing the control module to control such vehicle;
the control module operative to assume control of such vehicle when it sends such pulse trains.

14. The sleep apnea, snoring, emergency situations and breath assistance device of claim 13, wherein the communication protocol further comprises one member selected from the group consisting of: V2X, Bluetooth, WiFi, and combinations thereof.

15. The sleep apnea, snoring, emergency situations and breath assistance device of claim 10, configured for use by such person in a job requiring attention and focus.

16. The sleep apnea, snoring, emergency situations and breath assistance device of claim 5, further comprising:
at least one blood pressure sensor, the blood pressure sensor in operative communication with the control module, the blood pressure sensor configured to be disposed on such skin of such person;
the control module further comprising an analysis module operative to receive a data from the blood pressure sensor and analyze the data to determine if such person is exhibiting normal autonomic breathing and if sch person is not exhibiting normal autonomic breathing, the control module further operative to send the pulse trains.

17. The sleep apnea, snoring, emergency situations and breath assistance device of claim 5, further comprising:
at least one sensor of at least one heart rate sensor, the heart rate sensor in operative communication with the control module, the heart rate sensor configured to be disposed on such skin of such person;
the control module further comprising an analysis module operative to receive a data from the heart rate sensor and analyze the data to determine if such person is exhibiting normal autonomic breathing and if such person is not exhibiting normal autonomic breathing, the control module further operative to send the pulse trains.

* * * * *